United States Patent
Simonyi et al.

(10) Patent No.: US 10,960,393 B2
(45) Date of Patent: Mar. 30, 2021

(54) APPARATUS AND METHODS FOR BIOPROCESSES AND OTHER PROCESSES

(71) Applicant: IDEX Health and Science LLC, Rohnert Park, CA (US)

(72) Inventors: Victor Simonyi, Healdsburg, CA (US); Darrin Kurt Pickle, Santa Rosa, CA (US); James Smyth, Santa Rosa, CA (US); Craig Love, Santa Rosa, CA (US)

(73) Assignee: IDEX HEALTH AND SCIENCE LLC, Rohnert Park, CA (US)

( * ) Notice: Subject to any disclaimer, the term of this patent is extended or adjusted under 35 U.S.C. 154(b) by 148 days.

(21) Appl. No.: 16/108,008

(22) Filed: Aug. 21, 2018

(65) Prior Publication Data

US 2019/0060896 A1 Feb. 28, 2019

Related U.S. Application Data

(63) Continuation-in-part of application No. 15/683,235, filed on Aug. 22, 2017, now Pat. No. 10,711,237.

(51) Int. Cl.
*B01L 3/00* (2006.01)
*C12M 1/34* (2006.01)

(52) U.S. Cl.
CPC ..... *B01L 3/502715* (2013.01); *B01L 3/50273* (2013.01); *C12M 41/32* (2013.01); *B01L 2300/0627* (2013.01); *B01L 2300/14* (2013.01)

(58) Field of Classification Search
CPC ...... C12M 41/00; C12M 41/30; C12M 23/52; C12M 23/28; C12M 23/40; C12M 23/44; C12M 29/04; C12Q 1/02
See application file for complete search history.

(56) References Cited

U.S. PATENT DOCUMENTS 4,888,295 A 12/1989 Zaromb et al.
6,155,123 A 12/2000 Bakalyar
(Continued)

OTHER PUBLICATIONS

International Search Report and Written Opinion, PCT/US 18/47394, dated Dec. 21, 2018.
(Continued)

*Primary Examiner* — Michael L Hobbs
(74) *Attorney, Agent, or Firm* — Kilpatrick Townsend & Stockton LLP

(57) ABSTRACT

Apparatus and methods for providing a single-use, disposable module or manifold for testing and analysis of bioprocesses, as well as a portable and compact device which can be used with the module or manifold. A module comprising a valve, a filter or guard column, an affinity column, and a flow cell is provided with several ports for receiving tubing connections for a sample and one or more solvents, as well as one or more outlet ports for connections to one or more waste reservoirs. The flow cell may use UV light to determine a protein concentration of a sample in one particular example. The module can be connected directly or indirectly to a bioreactor containing the bioprocess and material to be sampled, and can be disposed of once a production run has been completed. In addition, manifolds are provided which can be embodied as a valve assembly, and which can comprise the same components and features as the disposable module. The manifolds and modules are compact and easy to use. A portable device adapted for use with a easily removable module is also provided.

40 Claims, 30 Drawing Sheets

(56) References Cited

U.S. PATENT DOCUMENTS

| | | | |
|---|---|---|---|
| 7,217,367 B2 | 5/2007 | Huang et al. | |
| 8,512,566 B2 | 8/2013 | Griffin et al. | |
| 2002/0146817 A1* | 10/2002 | Cannon | C12M 29/10 435/289.1 |
| 2006/0201263 A1 | 9/2006 | Furey et al. | |
| 2010/0077874 A1 | 4/2010 | Kanomata | |
| 2010/0210008 A1 | 8/2010 | Strand et al. | |
| 2011/0045599 A1 | 2/2011 | Erickson et al. | |
| 2011/0070654 A1 | 3/2011 | Tukhtuev et al. | |
| 2011/0189715 A1 | 4/2011 | Likuski et al. | |
| 2012/0138173 A1 | 6/2012 | Cirou et al. | |
| 2012/0327397 A1 | 12/2012 | Tormod | |
| 2015/0175950 A1* | 6/2015 | Hirschel | C12M 29/04 435/239 |
| 2015/0190809 A1 | 7/2015 | Tuccelli et al. | |
| 2016/0139094 A1* | 5/2016 | Hartmann | G01N 30/20 137/625.46 |

OTHER PUBLICATIONS

U.S. Appl. No. 15/683,235 , Final Office Action, dated Jan. 17, 2020, 10 pages.

U.S. Appl. No. 15/683,235 , Non-Final Office Action, dated May 28, 2019, 14 pages.

U.S. Appl. No. 15/683,235 , Notice of Allowance, dated Mar. 13, 2020, 9 pages.

\* cited by examiner

SECTION A-A

SECTION B-B

SECTION C-C

SECTION D-D

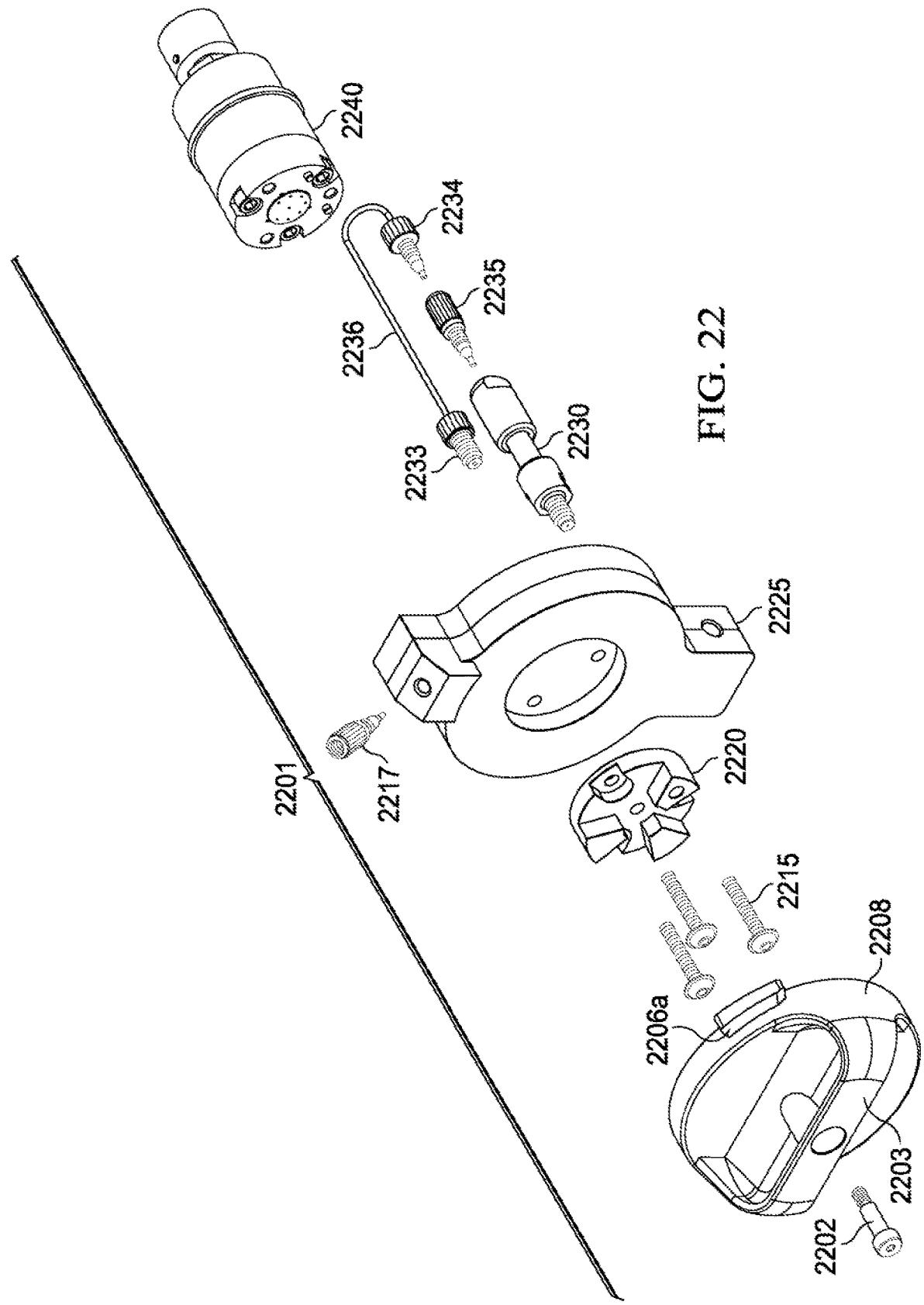

APPARATUS AND METHODS FOR BIOPROCESSES AND OTHER PROCESSES

RELATED APPLICATIONS

This application is a continuation-in-part of and claims the benefit of priority of U.S. patent application Ser. No. 15/683,235, filed on Aug. 22, 2017, which is hereby incorporated by reference as if fully set forth herein.

FIELD OF THE INVENTION

The invention relates to apparatus and methods for use in the bioprocess industry, and more particularly to disposable modules and manifolds useful for monitoring and analyzing bioprocesses, such as, for example, monitoring protein concentrations, and methods of using the same.

BACKGROUND OF THE INVENTION

In bioprocesses, such as during the development and manufacture of biologics and biosimilars, it is often necessary to monitor protein concentration (e.g., measurement of the protein titer) during the course of a production run to ensure product quality and maximize the yield of that production run. Typically, a production run is currently run as a batch process in a bio-reactor vessel (sometimes referred to as a bioreactor). In such production runs, the protein concentration versus time usually can be modeled as an exponential growth followed by a decay curve. The closer the manufacturer can come to ending the production run at this inflection point, the more efficient the production run and the subsequent steps in the process can be. Monitoring protein concentration can be a critical parameter in monitoring the production run. Given that a single batch of protein can be worth millions of dollars, it is critical that this growth is monitored in order to maximize the yield of each production run.

In such bioprocesses, samples are typically taken at the bio-reactor vessel and then moved to an onsite quality control lab for testing and analysis. A typical QC lab at a bioprocess facility is located in a different room than the bio-reactor vessel and has a backlog of samples for analysis. In addition, it is often a separate group within a given organization that will be performing the analysis. Often, the backlog of samples for testing is such that the analysis of a sample may not be completed for one or two days or so after the sample was taken. This situation creates a challenge for the manufacturers as they may be making decisions with respect to the production run based on old data. Furthermore, this approach and lab system typically requires a highly skilled individual (usually someone with a graduate level degree or perhaps a bachelor's degree with several years of relevant experience) to perform the analysis.

Once a production run in such a bioprocess is complete, a changeover step is usually required next, during which the manufacturing equipment is thoroughly cleaned and prepared for the next production run. Because the production of biologics and biosimilars is usually a very sensitive process, small amounts of any contamination can cause an entire production run to be scrapped, thereby resulting in a loss of potentially millions of dollars to the manufacturer. To ensure cleanliness, time consuming cleaning steps are typically written into manufacturer standard operating procedures. Any manufacturing or equipment component that comes into contact with the product must be thoroughly cleaned. Due to the risks and costs of any contamination, in addition to the cost of cleaning, and the time required for such cleaning, disposable devices (sometimes referred to as single use devices) have been increasingly considered for use in the industry. In addition, as the bioprocess industry matures, there has been a shift in the skill level of many production personnel, with the result that many processes and activities previously done by individuals with extensive skill and advanced degrees are in many situations done today by less educated technicians.

Conventional approaches have included various apparatus and methods for bioprocesses, which include US published patent application no. 2012/0138173 A1, entitled "Device For A Biological Liquid Treatment Installation", with named inventors Sebastien Cirou, Rene Reinbigler, Virginie Buisson, Jean-Louis Weissenbach, which was published on Jun. 7, 2012 and describes a device comprising a base (2) and a door (20), said device having a closed door position in which a circuit (8) of the device comprises a bag comprising two flexible films and connectors of the conveying network, and a press (9) comprising a first shell (16) disposed on a front face (5) of said base (2) and a second shell (17) disposed in said door (20); and a hinge system hinging said door (20) relative to said base (2), and disposed only on one side of said door (20) so as to form lateral clearances between said door (20) and said base (2) over the rest of a perimeter of said door (20).

In U.S. Pat. No. 7,217,367 B2, entitled "Microfluidic chromatography," issued to Jiang Huang, Hou-Pu Chou, and Marc A. Unger on May 15, 2007, a microfluidic chromatography apparatus is disclosed which comprises a microfabricated fluid delivery system and a chromatography column which is in fluid communication with the fluid delivery system, and a method for producing and using the same.

A disposable fluid path is described in U.S. Pat. No. 8,512,566 B2, entitled "Disposable fluid path systems and methods for processing complex biological materials," issued to Weston Blaine Griffin, Jaydeep Roy, Eric Douglas Williams, Phillip Alexander Shoemaker, and James Mitchell White on Aug. 20, 2013. This patent describes a disposable fluid path for processing complex materials that comprises a gravity assisted disposable system for separating a biological sample into two or more distinct submaterials through sedimentation. The fluid path is comprised of a sample delivery conduit and bag-set wherein the bag set comprising a tubing assembly, a separation assembly, and a filter assembly. Methods of using the system are also disclosed.

A fluid sampling device is disclosed in US published patent application no. 2006/0201263 A1, entitled "Disposable, pre-sterilized fluid receptacle sampling device," with named inventors James Furey, and Stephen Proulx, published on Sep. 4, 2006. In this patent application, a fluid sampling device comprising a port insert, a plurality of flexible conduits, and a plurality of sample containers is described, with the port insert having a body having a plurality of shafts therethrough and a rotatably displaceable member for individually opening and closing any of said shafts to enable the flow of fluid there through. Flexible conduits (e.g., flexible tubing) are equal in number to the shafts, with each flexible conduit connected to or otherwise in fluid communication with an individual shaft. Similarly, sample containers (e.g., flexible bags) are equal in number to the conduits, with each sample container connected to an individual conduit opposite the connection to the shaft. A specific configuration for the port insert, as well as kit containing sterilized components of the fluid sampling device, is also described.

U.S. Pat. Nos. 8,512,566 and 7,217,367, and United States published patent application nos. 2012/0138173 and 2006/0201263, are hereby incorporated by reference as if fully set forth herein.

SUMMARY OF THE INVENTION

Apparatus and methods for providing a single-use, disposable module or manifold and related apparatus and methods for testing and analysis of biological processes and other processes are disclosed and described. In one embodiment of the present disclosure, a module comprising a valve, a filter or guard column, an affinity column, and a flow cell is provided with several ports for receiving tubing connections for a sample and one or more solvents, as well as one or more outlet ports for connections to one or more waste reservoirs. The flow cell may use UV light to determine a protein concentration of a sample in one particular example. The module can be connected directly or indirectly to a bioreactor containing the bioprocess and material to be sampled, and can be disposed of once a production run has been completed.

In other embodiments of the present disclosure, manifolds are provided which can be embodied as a valve assembly or a portion of a valve assembly, and which can comprise some or all of the same components and features as the disposable module described herein. As will be apparent from the more detailed description to follow, the manifolds and modules disclosed herein can be compact and easy to use. In yet another embodiment of the present disclosure, a portable device for use with a removable module is also provided and disclosed.

In one embodiment of the present disclosure, a single use module for analysis of a bioprocess is provided, with the module comprising a housing having a plurality of inlet ports and a plurality of outlet ports, wherein said housing has a flow cell therein or extending at least partially from one side thereof, a valve located at least partially in said housing, and a column located in said housing, wherein said housing is adapted to receive a biological sample through a sample inlet port in one side thereof, and, when a solvent is pumped under pressure into said housing, move through the column and the flow cell, and wherein the flow cell is adapted to determine a characteristic of the sample. The module may be designed to test and analyze one or more of a variety of characteristics of the sample, such as protein concentration, spectral information, fluorescence, or a combination thereof. The module may have a column which may comprise any one of the following: affinity column, or chromatographic media. The module may have one or more removable sides, but in other embodiments may be designed so that none of the sides are easily removed and in fact may be designed and built so that the module is tamper-resistant. The module may have at least one sample inlet port, at least one solvent inlet port, and at least one waste outlet port. The module may also have a filter located wholly or partially therein, with the filter located in the fluid pathway, and the filter may comprise a filter, a frit, and/or a guard column, or a combination thereof. In one embodiment, the module may have the sample inlet port, the column, the flow cell, and the valve define a fluid pathway through said module, and wherein the materials which define the fluid pathway all comprise biocompatible materials. In addition, the module may have a flow cell that comprises an ultraviolet source and an ultraviolet detector. The module may be designed and build so that it operates without leaking or extrusion of any tubing with fluid pressures of up to at least 500 psi, up to at least 6,000 psi, up to at least 9,000 psi, up to at least 15,000 psi, or up to at least 20,000 psi.

In another embodiment of the present disclosure a device for a biological process is disclosed, with the device comprising a device adapted to be removably connected to an outlet from a bioreactor vessel containing a biological process, wherein said device is further adapted to removably hold a module having an inlet in fluid communication with the outlet from said vessel, wherein said module comprises a housing having at least one inlet port and at least one outlet port, wherein said housing has a flow cell therein or extending at least partially from one side thereof, a valve located at least partially in said housing, and a column located in said housing, wherein said housing is adapted to receive a biological sample through a sample inlet port in one side thereof, and, when a solvent is pumped under pressure into said housing, move through the column and the flow cell, and wherein the flow cell is adapted to be connected to at least one or more instruments for determining a characteristic of the sample, and wherein said module is adapted to be removably held in a portion of said device. The portion of said device adapted to removably receive and/or hold a module may comprise an extendable drawer of said device. The device may have the inlet port, flow cell, column, and sample inlet port connected by tubing within said module, and may comprise one or more biocompatible materials. The device maybe adapted so that the one or more characteristics of the sample to be tested and/or analyzed comprise protein concentration, spectral information, fluorescence, or a combination thereof.

In another embodiment of the present disclosure, a manifold comprising at least one inlet port and at least one outlet port, wherein said manifold has a flow cell and a column located therein, and fluid pathways in fluid communication with the flow cell and the column that are adapted to be connected to a portion of a valve, wherein said manifold is adapted to receive a biological sample through a sample inlet port in one side thereof, and, when a solvent is pumped under pressure into said manifold, move through the column and the flow cell. The portion of said valve of the manifold may comprise a valve stator, a valve rotor, a valve rotor seal, or a combination thereof. The flow cell of the manifold may be adapted to be connected to an ultraviolet source and an ultraviolet detector. The manifold may define a fluid pathway that includes the flow cell and the column, and may comprise one or more biocompatible materials. The manifold may be adapted to test one or more samples provided thereto for any one of the following: protein concentration, spectral information, or structural information, or a combination thereof. In addition, the manifold may be adapted to operate with fluid pressures up to at least 500 psi, up to at least 6,000 psi, up to at least 9,000 psi, up to at least 15,000 psi, or up to at least 20,000 psi. The manifold may comprise a unitary piece, or may comprise two or more pieces joined together. In addition, the manifold comprises a substantially rectangular prism shape, a substantially cylinder shape, or any other shape that may be desired. The manifold may include ports for removably receiving tubing to provide fluid flowpaths external to the manifold and/or internal channels or passageways to provide fluid pathways internal within the manifold.

In yet another embodiment of the present disclosure, a method for monitoring a biological process is disclosed that comprises connecting an outlet from at least one bioreactor containing a biological process, directly or indirectly, to a sample inlet of a first module, wherein the first module may comprise a flow cell, a valve, and/or a column therein, and the first module is adapted for use with a single production batch of the bioreactor, providing a sample from the at least one bioreactor to the first module, analyzing the sample with the first module, repeating the steps of providing a sample and analyzing the sample, as desired, disconnecting the first module from the at least one bioreactor when one or more characteristics of the biological process in the at least one bioreactor have been determined, and/or when the production run in the bioreactor is deemed to be completed. The method may further comprise the step of connecting a second module to the device when the at least one bioreactor is to be used for a second batch of a biological process, wherein the second module comprises a flow cell and a column substantially the same as that of the first module. In addition, the method may include connecting an outlet from a second bioreactor, directly or indirectly, to an inlet of the first module, providing a second sample from the second bioreactor to the first module, analyzing the second sample with the first module, repeating the steps of providing a sample and then analyzing each sample as desired, and disconnecting the first module from the second bioreactor when one or more characteristics of the biological process in the second bioreactor have been determined, and/or when the production run in the bioreactor is deemed to be completed, and/or connecting a second module to the device when the at least one bioreactor is to be used for a second batch of a biological process, wherein the second module comprises a flow cell and a column, at least one of which is of a different kind than the flow cell or column of the first module. The method may also include the step of connecting a second module to the device when the at least one bioreactor is to be used for a second batch of a biological process, wherein the second module comprises a flow cell and a column, at least one of which is of a different kind than the flow cell or column of the first module. The methods may be performed automatically and under the control of a control system, which may also control a fluid engine and a sampling system in combination with a module.

In another embodiment of the present disclosure a portable device for testing and/or analysis is provided and may include a portable device for a testing samples comprising a device adapted to be removably connected to a sample source, wherein said device is further adapted to removably hold at least one solvent container in a first portion of said device and removably hold a module in a second portion of said device, wherein the module has an inlet for receiving a sample from the sample source, and wherein said module comprises a housing having at least one inlet port, wherein said housing has a flow cell therein or extending at least partially from one side thereof, a valve located at least partially in said housing, and a column located in said housing, wherein said housing is adapted to receive a sample through a sample inlet port in one side thereof, and, when a solvent is pumped under pressure into said housing, move through the column and the flow cell, and wherein the flow cell is adapted to be connected to at least one or more instruments for determining a characteristic of the sample. The portable device may include tubing connecting the inlet port, flow cell, column, and/or sample inlet port may comprise one or more biocompatible materials. In addition, the portable device may be adapted to test or analyze a characteristic of a sample, wherein the characteristic of the sample comprises: presence and amount of one or more chemicals, protein concentration, spectral information, fluorescence, or a combination thereof. The portable device, together with the module and the solvent container, may be adapted to weigh from about 5.5 Kilograms to about 22 Kilograms, with the solvent container substantially full with liquid. The portable device may also weigh less, such as three kilograms to about fifteen kilograms. The portable device may further comprise a handle on one surface thereof. In addition, the portable device may have the module further adapted to be connected to a control system, or may itself contain a control system, wherein the control system may be further connected to a sampling system, a sample source, or a combination thereof. In one embodiment, the device may also include a control system having at least one processor, memory coupled thereto, and computer software stored in memory with instructions executable by the processor to perform automated sampling, testing, analysis, and then provide (e.g., display or output) and/or store the results of the analysis. The device may include one or more input/output devices or connections for such devices, including but not limited to a display for displaying information and/or receiving input from a user, a touch panel (which may be part of the display) which a user can use to input information and control the operation of the device and the control system, such as by inputting information or selecting parameters such as User ID, Sample ID, Calibration Curve, and the like, a USB port or other port for receiving or outputting information or data, a printer, and/or a connection for sending and/or receiving information wirelessly, such as via a WiFi connection or a cellular or other connection. The device may further include a fluid engine, with the control system programmed to also control the fluid engine operations and components, as well as the components of the module when the module is connected to the device.

In one embodiment, the module may be a purpose-built system, wherein the module comprises a single-use module that is designed and built to perform a single type of test or analysis, and/or to perform a single type of method, repeatedly, and then be disposed of after the intended tests, analyses, or methods have been performed. It will be appreciated that an advantage of such a module is that it allows for a great deal of flexibility, wherein one or more of the components therein can be made of different sizes and/or materials to allow the module to perform different intended applications. In addition, the module can include one or more different components, or may omit one or more different components, from a given design, such that the different module can be used for a different intended application.

In one embodiment, the present disclosure includes a module for analysis of a sample, with the module comprising: a valve having a stator with a first plurality of openings on one side thereof; a column having a first end and a second end; and a manifold having a first side and a second side, wherein the first side has a second plurality of openings, each corresponding to one of the plurality of first openings, and the first side has a third plurality of openings, with at least one of the third plurality of openings in fluid communication with the second end of the column and at least another one of the third plurality of openings in fluid communication with one or more of a solvent source and a waste receptacle, and wherein the manifold further comprises a flow cell and has first and second flow cell openings, wherein the first flow cell opening in the manifold is adapted to receive a source input to the flow cell and the second flow cell opening is adapted to receive a detector input to the flow cell, and wherein the module is adapted to be removably attached wholly or partially to a device. The flow cell may be adapted to be connected to at least one or more instruments for determining a characteristic of the sample, wherein the characteristic of the sample may comprise: protein concentration, spectral information, fluorescence, or a combination thereof. The module may further comprises biocompatible fluid pathways therein, and/or may be adapted to be connected to a control system when attached to the device. In addition, the module may be adapted to fit at least partially in a nest of the device, and the nest may be hinged, comprise a drawer, or some other recess or portion of the device. If desired, the module may be removably secured at least partially or wholly within a nest of the device. The module may weigh from about 0.3 Kilograms to about 3 Kilograms, and may weigh no more than 0.5 Kilograms, no more than 1 Kilogram, and/or no more than 2 Kilograms. The module may be adapted to operate with fluid pressures up to 500 psi, 6,000 psi, 9,000 psi, 15,000 psi, or 20,000 psi.

In another embodiment, the present disclosure provides a device comprising a housing having external surfaces, a valve having a stator with a first plurality of openings on one side thereof, wherein the valve may be mounted wholly or partially within the housing, and a manifold having a first side and a second side, wherein the first side has a second plurality of openings, each corresponding to one of the first plurality of openings, and the second side has a third plurality of openings, with at least one of the third plurality of openings adapted for fluid communication with one end of a column when a column is removably coupled or attached to the manifold, and at least another one of the third plurality of openings adapted to be in fluid communication with one or more of a solvent source and a waste receptacle, and wherein the manifold further comprises a flow cell and has first and second flow cell openings, wherein the first flow cell opening in the manifold is adapted to receive a source input to the flow cell and the second flow cell opening is adapted to receive a detector input to the flow cell, wherein the second side of the manifold is adapted to be removably coupled or attached wholly or partially to a guard column or a column, and wherein the manifold may be located wholly or partially within a housing of a device, and either or both of the valve may be mounted to provide a portion or surface having one or more openings adapted for one or more fluidic connections, such as with a guard column or a column. In one exemplary embodiment, one side of the manifold faces outwardly from the housing of a device, and a portion of the manifold may also extend outwardly from the housing surface.

SUMMARY OF THE DRAWINGS

FIG. 22 is an exploded view of an alternative embodiment of a module in accordance with the present disclosure.

DETAILED DESCRIPTION OF THE DISCLOSURE

Figure 1:
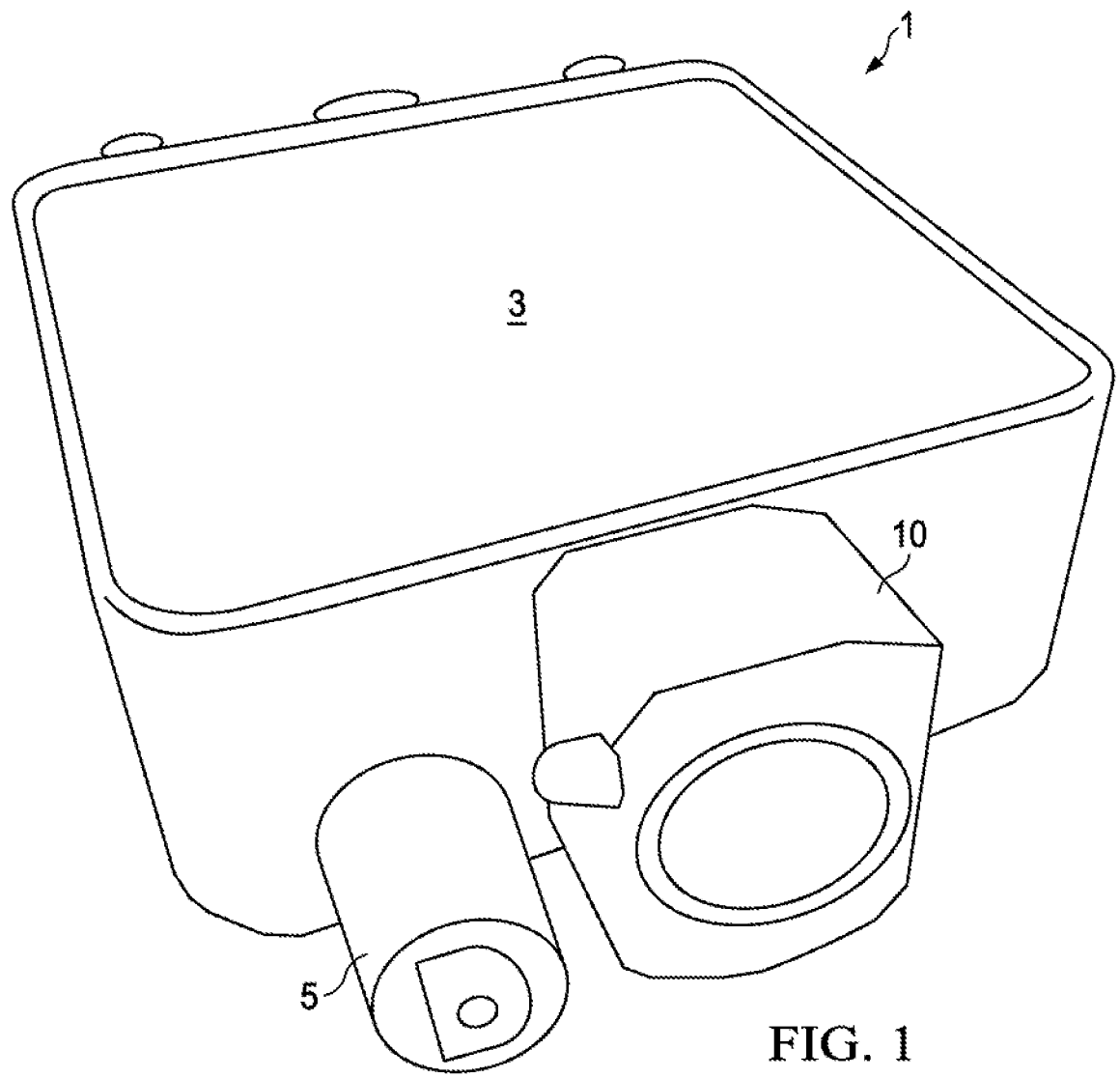
FIG. 1 is an isometric view of a disposable analytic module in accordance with one embodiment of the present disclosure.

Referring to FIGS. 1-4, one particular embodiment of a disposable, single-use analytical module 1 for use in bioprocesses is shown. In FIG. 1, the module 1 has a generally rectangular or square body 3 with rounded corners, a top and a bottom, as well as front and back faces. In FIG. 1, the front face of the module 1 has a flow cell 10 and a sample inlet port 5. The body 3 can be made of any one or a combination of a number of materials, such as plastics or polymers (including polypropylene, Delrin, and/or polyetheretherketone (PEEK)), and/or metals such as stainless steel, aluminum, polymers, plastics, or materials and the like.

Figure 2:
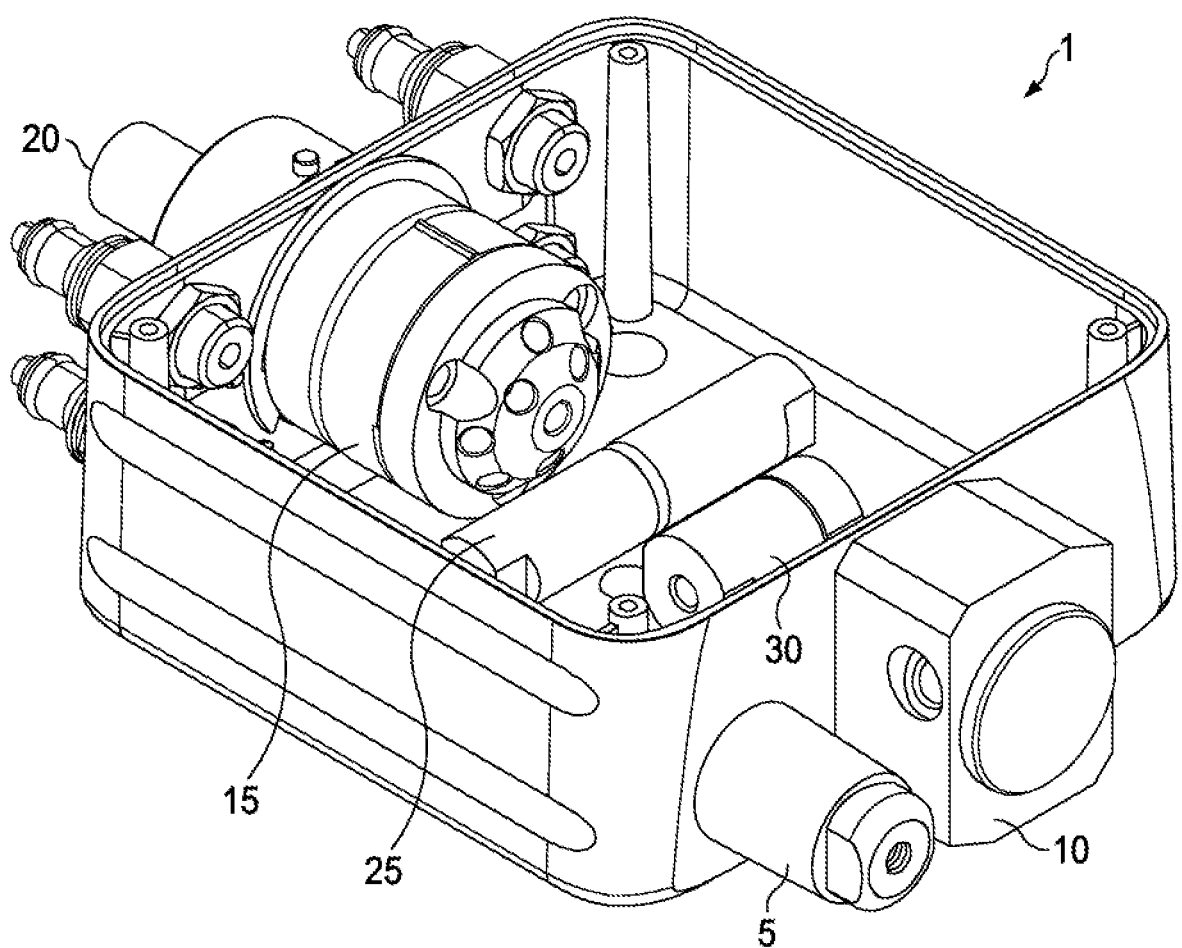
FIG. 2 is another isometric view of the disposable analytic module of FIG. 1.

In FIG. 2, the module 1 is shown in another isometric view, with the top removed. It will be appreciated that the numbering of various features shown in the drawings is the same for like features for convenience. As shown in FIG. 2, the module is shown with a flow cell 10 and a sample inlet port 5 on a front face. The back face of the module 1 includes a control shaft or handle 20 for a injector valve 15 (which can be, for example, a rotary shear valve). As shown in FIG. 2, the flow cell 10 and the valve 15 are attached to, respectively, the front and back faces of the module 1. In addition, the back face of the module 1 includes four fluidic connection ports. As also shown in FIG. 2, the module 1 includes a column 25 and a filter 30 therein. (The filter 30 can be any one of a number of different types of filters, such as a guard column, a frit, or another filter. The term "filter" as used herein will be understood by those skilled in the art to understand to refer to any such filtering means.) The valve 15, flow cell 10, filter 30, and column 25 can be connected in a fluid pathway as described in more detail below. It will be understood and appreciated that the module 1 can have more than one column 25 if desired, more than one filter 30 if desired, and can also be used without a filter 30 or column 25 if so desired for a particular application.

Figure 3:
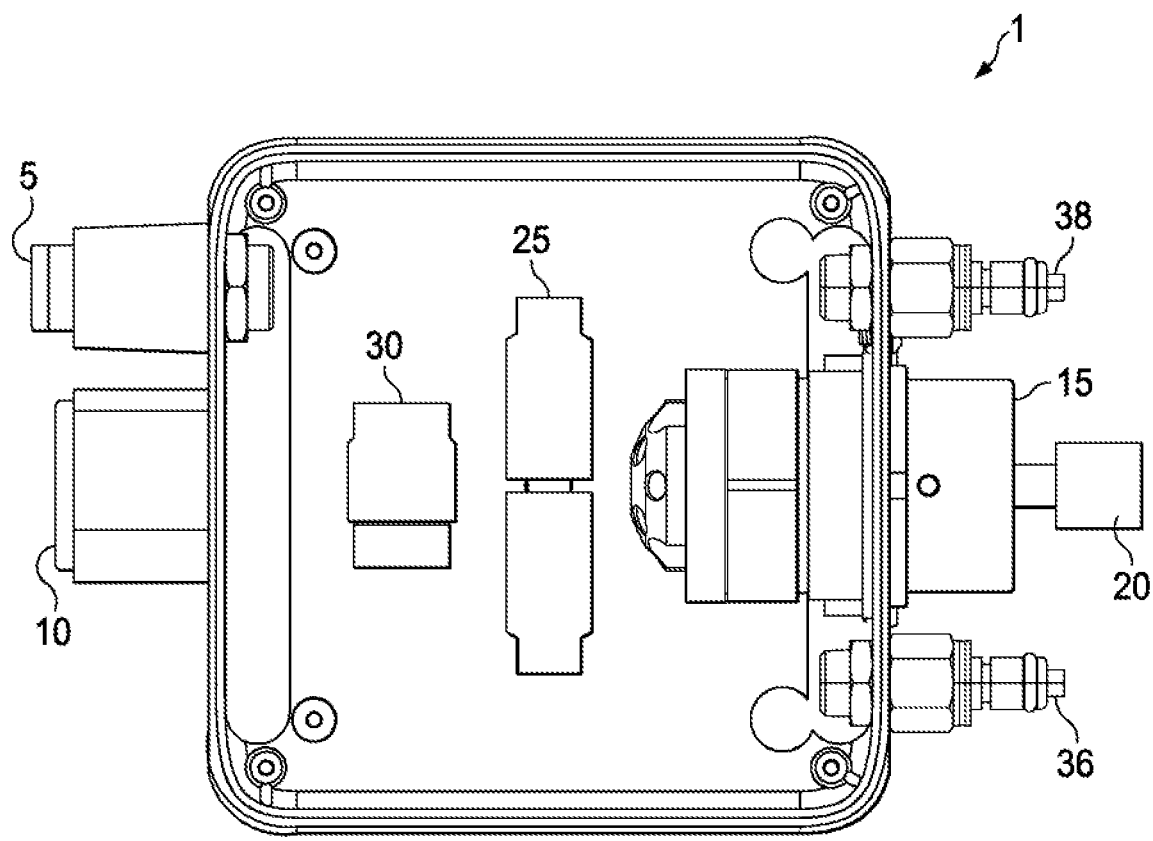
FIG. 3 is a top view of the disposable analytic module of FIGS. 1 and 2.

Now referring to FIG. 3, a top view of the module 1 (with the top removed) is shown. In this view, the flow cell 10, sample inlet port 5, filter 30, column 25, and valve 15 are shown. In addition, two of the four fluidic connection ports 36 and 38 are shown. Although FIG. 3 shows the top of the module 1 removed, it will be appreciated that in many applications, a removable top or other portion of module 1 is not desired. Indeed, in at least one particular embodiment of the present disclosure, the module 1 can be provided so that it is tamper-resistant, to thereby minimize the chance of reuse and possible contamination. However, those skilled in the art will also understand that a removable top cover of the module 1 may be provided if such is desired.

Figure 4:
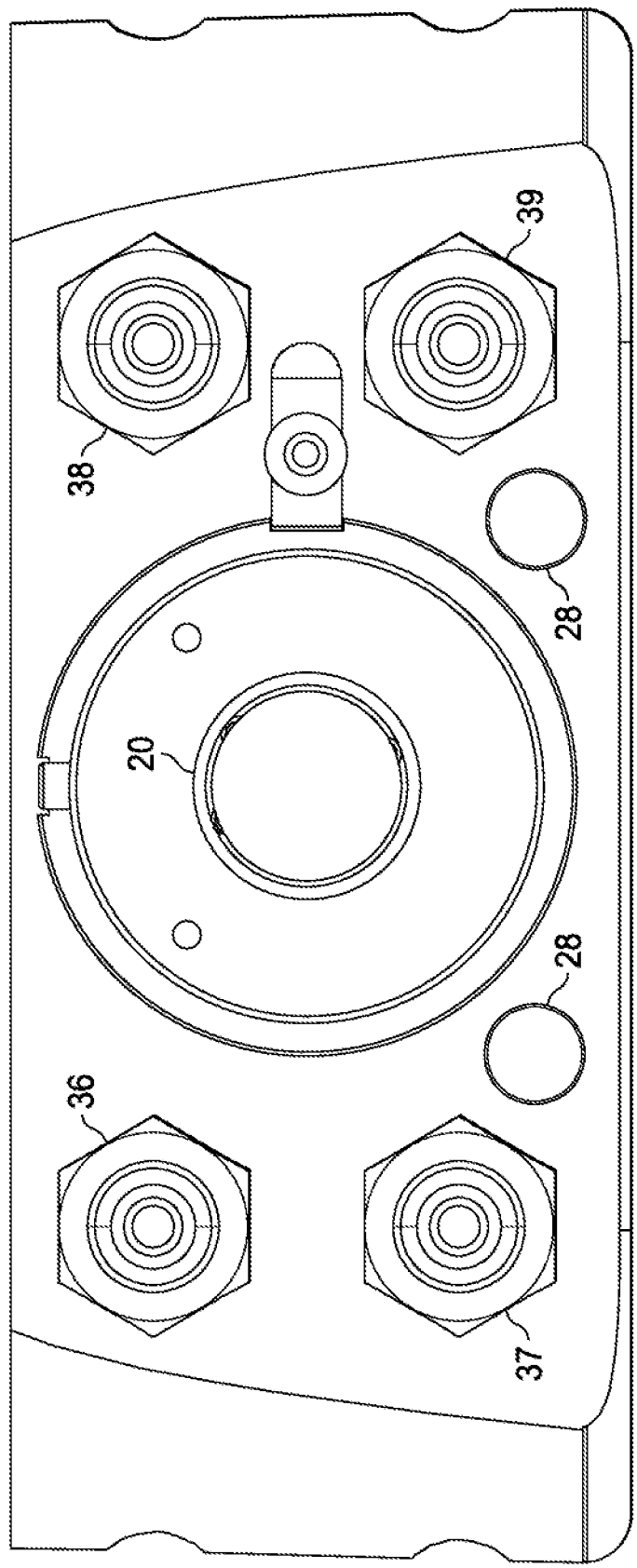
FIG. 4 is an enlarged partial end view of the disposable analytic module of FIGS. 1-3.

A partial view of the rear face of the module 1 is shown in FIG. 4. In FIG. 4, the shaft 20 of the valve 15 is shown, as are fluidic ports 36, 37, 38, and 39. Contacts 28 for LED illumination are also provided on the rear face of module 1. In one particular embodiment of a module 1 in accordance with the present disclosure, the fluidic ports 36-39 can be connected as follows: port 36 can be connected as a solvent B inlet, port 37 can be connected as a waste port, port 38 can be connected as a solvent A inlet port, and port 39 can also be connected as a waste port. The ports 36-39 can be any one of a number of types of standard ports adapted to removably and securely receive tubing for fluidic connections therein.

Figure 5:
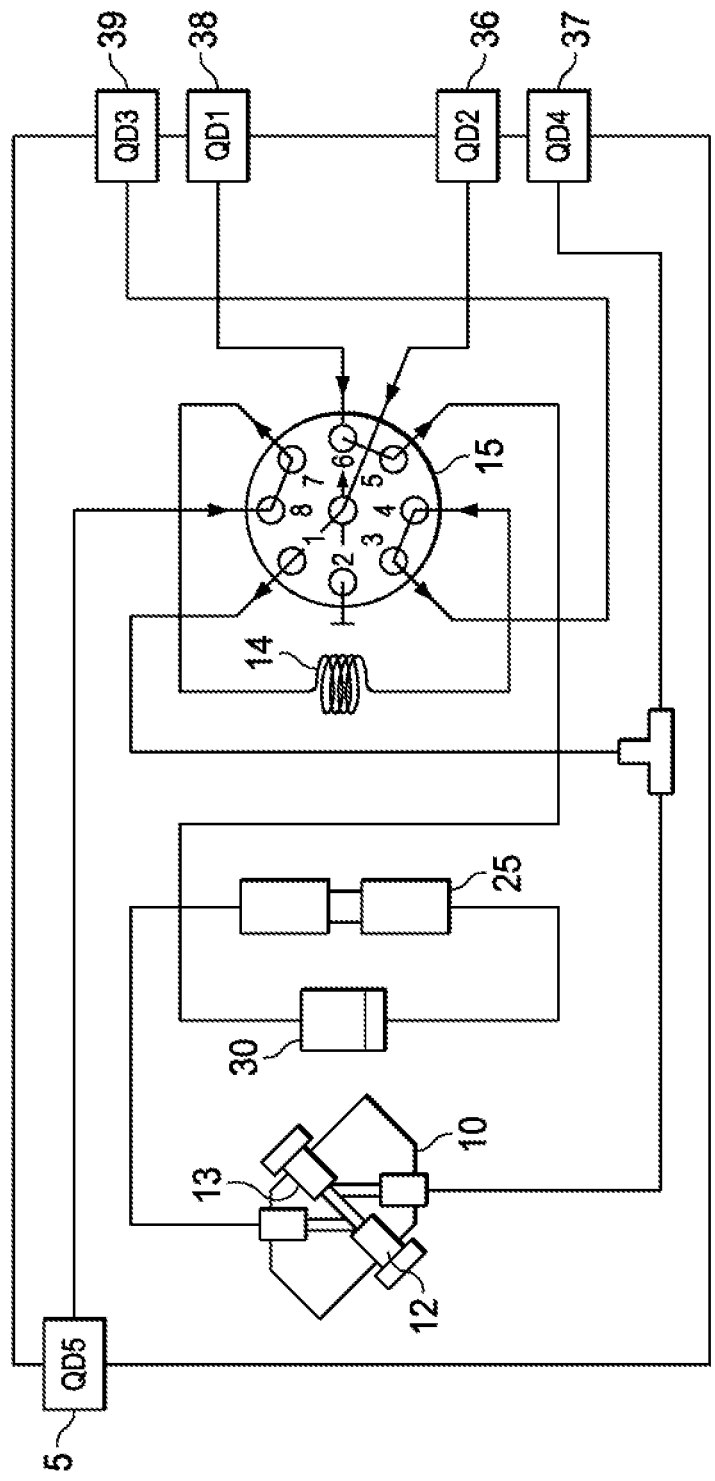
FIG. 5 is a schematic diagram of a disposable analytic module of one embodiment of the present disclosure.

FIG. 5 provides a schematic diagram of the fluidic connections and pathways in accordance with one potential embodiment of a disposable analytical module 1 in accordance with the present disclosure. As shown in FIG. 5, the module 1 has a sample inlet port 5 connection which is in fluid communication with one port of the valve 15 (in this particular example, port no. 8 of valve 15). Ports 7 and 4 of the valve 15 are connected to and in fluid communication with sample loop 14. Port 1 of the valve 15 and one of the connections of the flow cell 10 are connected to and in fluid communication with the waste port 37. Similarly, port 3 of the valve 15 is connected to and in fluid communication with the waste port 39. Port 5 of the valve 15 is connected to and in fluid communication with one end of the filter 30, and the other end of filter 30 is connected to an in fluid communication with column 25. The other end of the column 25 is then connected to and in fluid communication with flow cell 10. The solvent A inlet port 38 is connected to and in fluid communication with port 6 of the valve 15, and solvent B inlet port 36 is connected to and in fluid communication with port 9 of the valve 15.

The flow cell 10 in one particular embodiment can provide windows, ports, or openings 12 and 13 adapted and operable for connection to, respectively, an ultraviolet (UV) source and detector. In FIG. 5, the UV source port 12 and UV detector port 13 are not included as part of the flow cell 10. It will be appreciated that the ports, or windows 12 and 13, of the flow cell 10 may be adapted to be connected to fiber optic cables or the like, which in turn may be connected to a UV source and detector, respectively, especially when the UV source and/or detector are not included in or part of the flow cell 10 or module 1. Alternatively, it will be appreciated that a UV source and/or detector (not shown in FIG. 5) may be included in or a part of flow cell 10 and/or module 1. Those skilled in the art will appreciate that the UV source port 12 and detector port 13 can be connected to a controller (not shown) so that the information and signals from the source port 12 and detector port 13 are automatically provided to a controller, such as a computer, where the information can be stored, displayed, and used by the control system to perform other operations if desired. In one particular embodiment, the flow cell 10 may have a light source comprising an LED set to provide light with a wavelength of 280 nanometers, and may be connected to the source inlet of the flow cell 10 with a fiber optic cable. The UV light detector may comprise a photo diode detector, a Silicon Carbide (SiC) detector, or may be any one of a number of different types of detectors, with or without integrated amplifiers, or may be a UV diode-array detector. Those skilled in the art will further appreciate that, although a UV source opening 12 and detector opening 13 are included in flow cell 10, the flow cell 10 may include analytical instruments or may include other instruments different from a UV source and detector, such as, for example, any one or more of the following: RAMAN spectroscopy.

In operation, the module 1 works by having a sample from a bio-reactor vessel injected into a sample loop 14 located on or connected to the injection valve 15 in the module 1. When the injection valve 15 switches to the inject position, Solvent A forces the sample to flow out of the loop 14 and into the fluid path where it travels through the filter 30 and into an affinity column 25. At this point, the protein in the sample binds to the media in the column 25 and the remainder of the sample (known as the unbound) flows through the flow cell 10. The valve in the Fluidic Engine 3 of FIG. 6 and valve 15 switch to allow Solvent B to flow through the flow path of the module 1, which then releases the protein from the column media in column 25 and then flows through the flow cell 10 where it is analyzed. A user typically will sample a single batch multiple times throughout a Production Run. When a Production Run is completed, the user can easily replace the module 1 with another module, which may be a new and unused module of the same type or may be of a different type (e.g., having a different column, different flow cell, etc.).

The module 1 can be advantageous for a number of reasons. First, manufacturers currently need to draw a sample from a bioreactor tank or vessel, then transport this sample to a lab for analysis. These labs are often in a different location than the production floor and due to back logs, the labs could take hours or days to complete testing and provide results. The module 1 is capable of performing this sampling, testing and analysis while connected to a bioreactor vessel or tank (or any other source, for that matter) and can do such sampling, testing, and/or analysis in an essentially continuous manner once connected to a bioreactor vessel or tank, and can easily be located next to the bio-reactor vessel. Such an approach helps eliminate the potential for errors, such as errors in collection times, sample identification, and the like, and helps simplify the chain of custody which may be often required for each batch. In addition, this approach minimizes the chance of sample degradation or contamination, as well as providing greater assurance that the correct analytical method has been used for a given batch (since a module will likely be designed for one particular type of use, whereas a liquid chromatography system is typically used for a wide variety of samples tested with a variety of columns and other components). Second, all components of the module 1 that come into contact with the sample are contained within the module 1. This makes the changeover step from batch to batch very quick and easy. The user can simply disconnect and then remove the used single-use-module 1 and replace it with another. In the configuration illustrated, the user would only need to disconnect the following from the used module 1 and replace connections on the new module: Source, Detector, Solvent A, Solvent B, Sample in, valve waste, and flow cell waste. In addition, the module 1 helps avoid the use of more and longer fluid connections between different components for the analysis, thereby minimizing the potential for dead volumes or unswept volumes or locations in the system, as well as minimizing the potential for leaking or extrusion of tubing if a fluidic connection of tubing to a port is not made properly. This also helps minimize the potential for exposure to solvents used in the analysis. The module 1 can be designed so that it can be installed and connected (or disconnected, as the case may be) by hand and without the need for tools. The module 1 also avoids the potential problems which can arise when a human user installs a column in the system incorrectly (e.g., such as by installing the column contrary to its preferred flow direction).

Prototype testing has indicated that the module 1 may be around about 4 inches×4 inches×2 inches. In addition, we believe that the module 1 can be useful in testing samples with a range of a target of at least from 0.15 mg/ml to 10.0 mg/ml. It will be appreciated that the module 1 also provides the advantage of flexibility. For example, a given module 1 can be designed for operation with a target range up to 10.0 mg/ml as noted, such as for testing for protein concentration. However, the module 1 can be redesigned with a smaller sample loop and a smaller fluid pathway so that the redesigned module can be used to test for a target range of up to 200 mg/ml, such as for protein purification. Thus, it should be appreciated that the internal components and dimensions of the module 1 can be easily modified as desired to measure a broad range of parameters, such as protein concentrations. While many manufactures consider the ending concentration of a Production Run part of their proprietary manufacturing process, public documents indicate that they are producing titers up to approximately 3.0 mg/ml. We also believe that some manufacturers may be producing titers as high as 5.0 mg/ml with a goal of "as high as possible". We expect that the module 1 can measure such titer levels while providing the advantages noted.

Those skilled in the art will appreciate that the module 1 can be used with other fluidic connections and configurations. However, those skilled in the art will also appreciate that one advantage of the module 1 is that it can be configured so that it is ready for operation immediately once and an operator has connected tubing (not shown) to the sample inlet port 5, and solvent input ports 36 and 38, as well as waste ports 37 and 39, to the appropriate components of an existing system, such as connected port 5 to an output port of a bioreactor (not shown).

Figure 6:
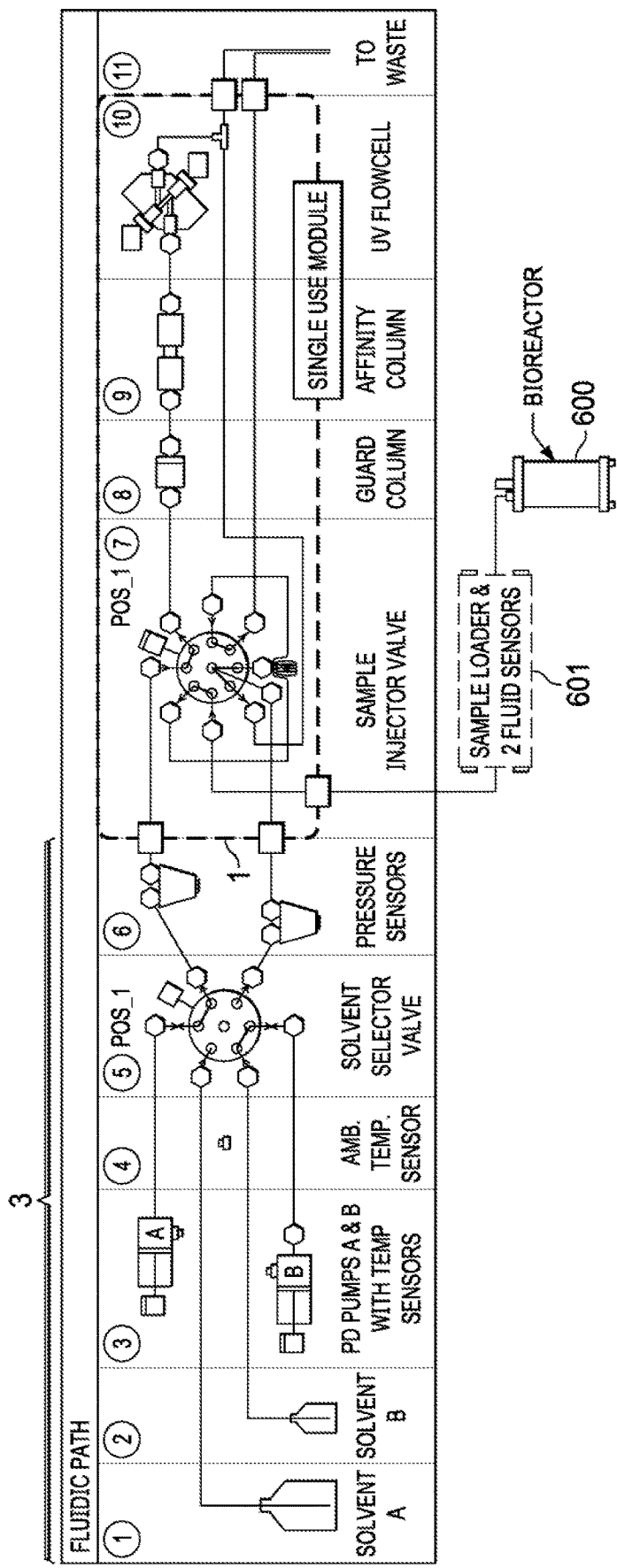
FIG. 6 is a schematic diagram of a disposable analytic module as connected to bioreactor in one embodiment of the present disclosure.

Turning now to FIG. 6, a schematic diagram of a fluidic pathway of fluidic connections in one particular configuration in accordance of the present disclosure is provided. The schematic diagram is divided into eleven distinct segments. In addition, the portion defined by dotted line 1 provides a schematic for a disposable module 1. The portion defined by the numeral 3 can be considered a fluidic engine. Also, shown schematically in FIG. 6 is a bioreactor vessel 600 and a combination of a sample loader and fluid sensor 601. As shown in FIG. 6, the bioreactor 600 is in fluid communication with the sample loader/sensor combination 601, which in turn is in fluid communication with at least one inlet of the module 1 and the valve in segment seven of the fluid path schematic. Those skilled in the art will appreciate that, although not shown in FIG. 6, the various valves, pumps, sensors, and other components of the system shown in FIG. 6 can be connected to a common control system (not shown) which can be programmed to run the testing of samples by module 1 automatically. Those skilled in the art will further understand and appreciate that the UV source and receiver elements may be connected to the same control system (not shown) to which the fluid engine 3 is connected, and the control system (not shown) typically includes one or more processors, memory, and computer instructions in the form of software which is executed by the processor to perform the steps described herein and to control the operation of the fluid engine 3, the UV source and detector, and the module, as well as to receive the information from the UV source and detector in operation and to output the results and data therefrom. The control system (not shown) may further have a display and/or a control panel for easy operation by a user.

Still referring to FIG. 6, in segments one and two, solvent sources A and B, respectively, are provided. As shown in FIG. 6, each of the solvent sources is connected to and in fluidic communication with one of the ports of the solvent selector valve of segment five after the fluid in the tubing passes through one or more sensors in segment four. Such sensor or sensors may be one or more fluid flow sensors, pressure sensors, motion sensors, temperature sensors, and the like, or a combination thereof. In segment three, pumps A and B are provided to pump the solvents A and B, respectively. The pumps A and B each may also contain one or more sensors. As shown in FIG. 6, pressure sensors can be provided in segment six to measure the pressure of the fluid flowing into the inlet ports of the module 1, with the inlet ports for the module 1 shown on the left side of segment seven in FIG. 6. In segment seven, the sample injector valve and its fluidic connections are shown. As indicated, at least one port of the selector valve is connected to an inlet of a filter, as shown in segment eight of FIG. 6. In addition, the outlet of the filter is connected to the inlet of a column in segment nine. The outlet of the column in segment nine is connected to an inlet of a flow cell in segment ten. In segment eleven, an outlet of the flow cell and an additional connection are connected to a waste reservoir.

Referring now to FIGS. 7A-7D and 8A-8D, a manifold 70 in accordance with one particular alternative embodiment of the present disclosure is provided. As will be appreciated from the description below and the accompanying figures, the manifold 70 can be provided as a disposable, single use module for providing an analytical analysis of a bioprocess, such as determining a protein concentration for example.

Figure 7A:
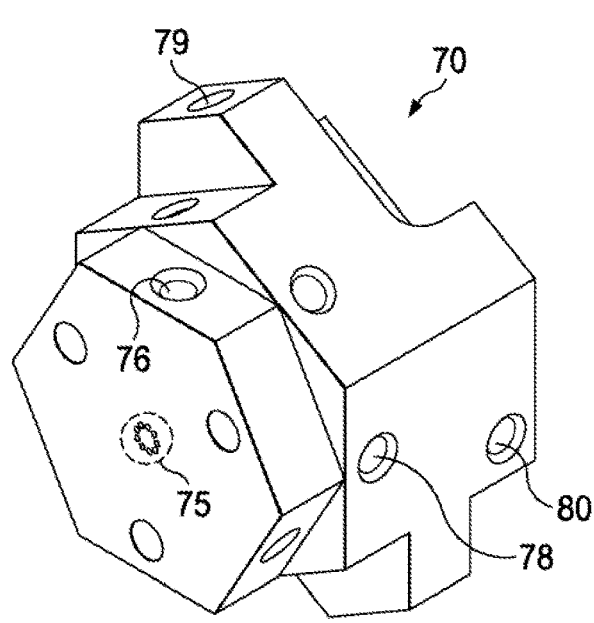
FIGS. 7A-7D are, respectively, an isometric view of a manifold module in accordance with one embodiment of the present disclosure, a top view of the manifold, a side view of the manifold, and a bottom view of the manifold.
Figure 7B:
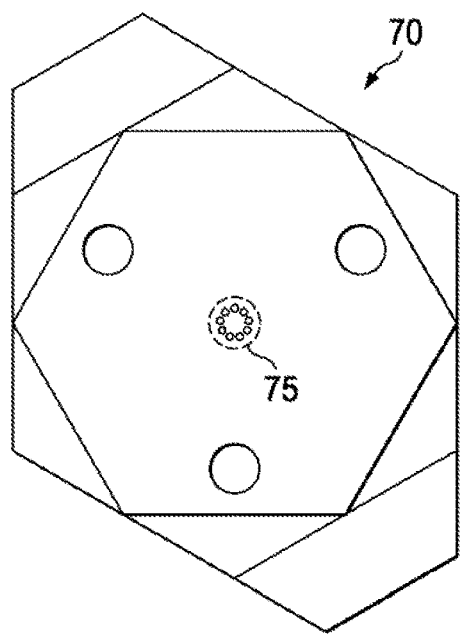
Figure 7C:
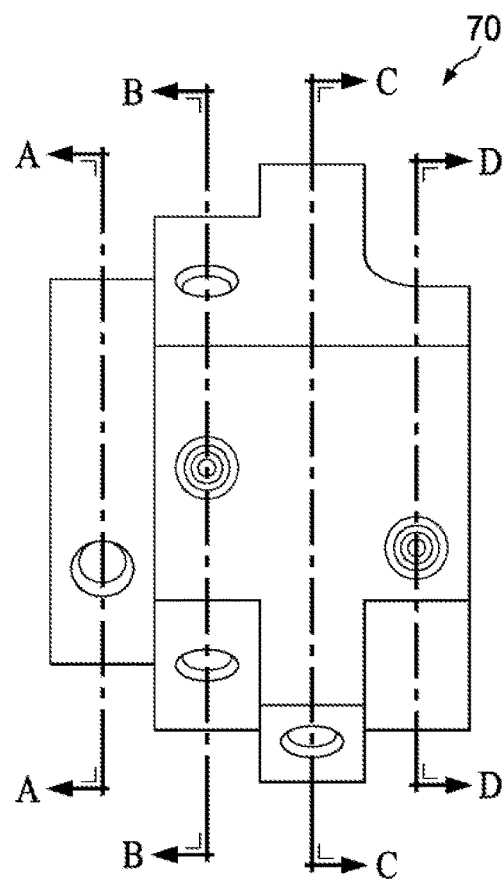
Figure 7D:
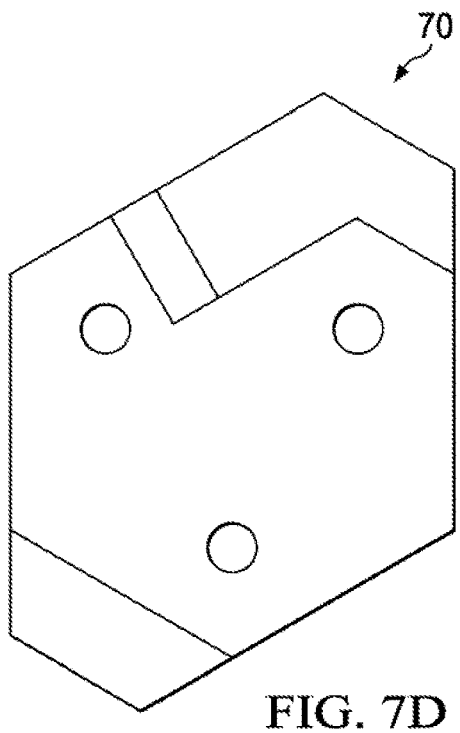

As shown in FIG. 7A, the manifold 70 has a first or top face or surface with a plurality of openings 75 therein. As indicated in FIG. 7C, the manifold 70 can be thought of as having four layers, each of which is shown in a cross-sectional view in FIGS. 8A-8D. As also shown in FIG. 7A, a first layer has a plurality of openings 76 therein on the sides of the layer, a second layer has a plurality of openings 78 therein on the sides of the second layer, a third layer has a plurality of openings 79 therein on the sides of the third layer, and a fourth layer has a plurality of openings 80 on the sides of the fourth layer.

Figure 8A:
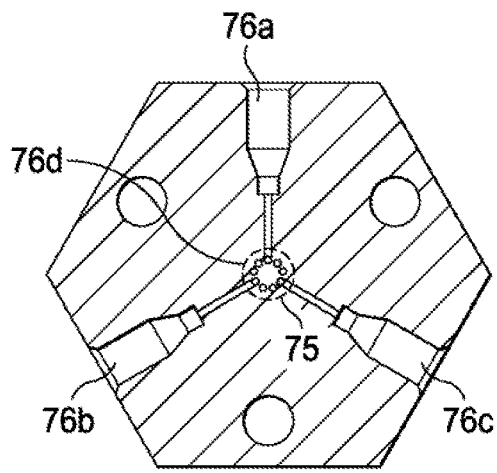
FIGS. 8A-8D are, respectively, cross-sectional views of the manifold of FIGS. 7A-7D taken along lines A-A, B-B, C-C, and D-D of FIG. 7C.
Figure 8B:
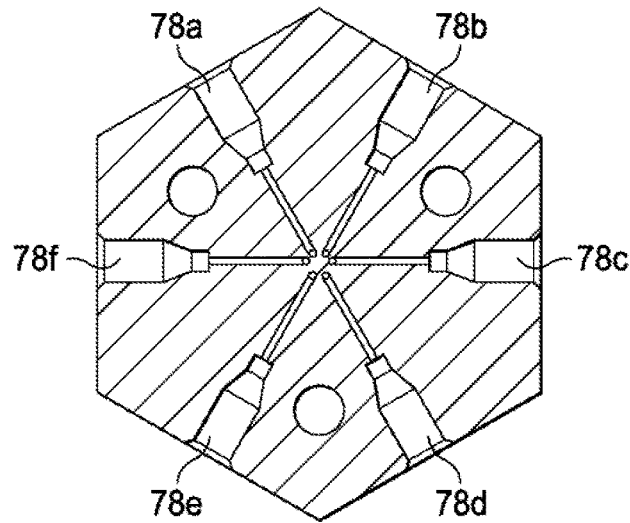
Figure 8C:
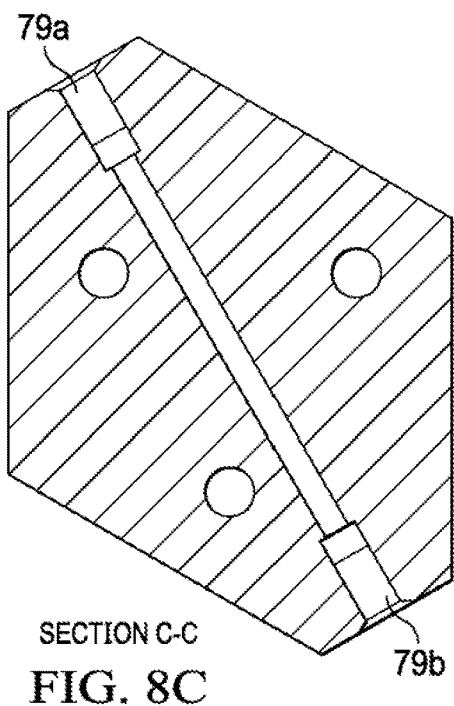
Figure 8D:
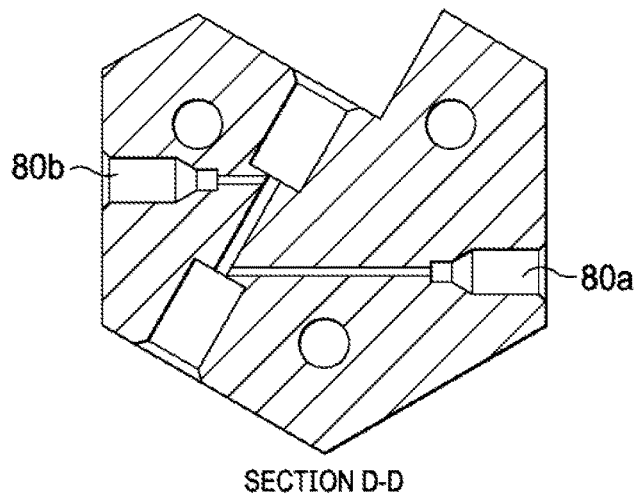

FIGS. 8A-8D provide cross-sectional views of the four different layers of the manifold 70 as taken along lines A-A, B-B, C-C, and D-D, respectively, as shown in FIG. 7C. In FIG. 8A, a first layer of the manifold 70 is shown in cross-section. This layer has three ports 76a, 76b, and 76c, as well as openings 76d. It will be appreciated that the openings 76d correspond to the openings 75 shown in FIG. 7A, so that, when the top face of the manifold 70 with the openings 75 is securely attached to a stator of a valve, fluid can flow through the valve stator, through openings 75, and through openings 76d as well. In FIG. 8B, a second layer of the manifold 70 is shown with six ports 78a-78f and fluid pathways therein which extend to the fluid pathways which extend to the plurality of openings 75 (with each fluid pathway shown in FIG. 8B in fluid communication with a corresponding one of the plurality of openings 75). In FIG. 8C, a third layer of the manifold 70 is shown and has two openings for ports 79a and 79b which are connected by a fluid pathway. It will be appreciated that the passageway between the ports 79a and 79b can be filled with a packing material or materials and can serve as a column for analytical purposes. In addition, FIG. 8D shows a fourth layer of the manifold 70 with two openings for ports 80a and 80b. It will be appreciated that the fourth layer as shown in FIG. 8D is configured to serve as a flow cell that can be used to sample, analyze and provide sample information, such as but not limited to protein concentration, spectral information (e.g., UV-Vis), near infra-red, and the like, or a combination thereof.

Figure 9:
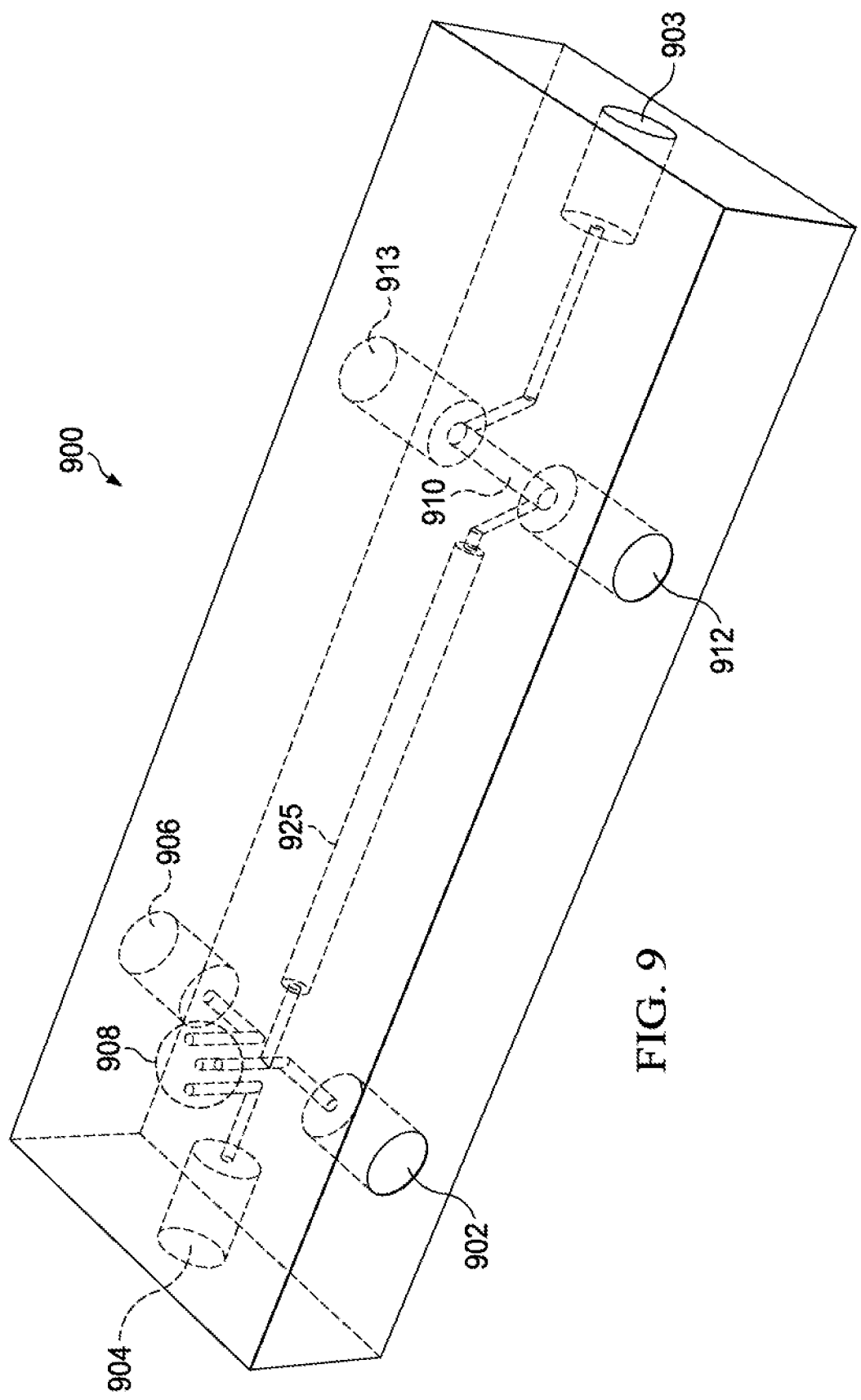
FIG. 9 is a view of an alternative module in accordance with one embodiment of the present disclosure.
Figure 10:
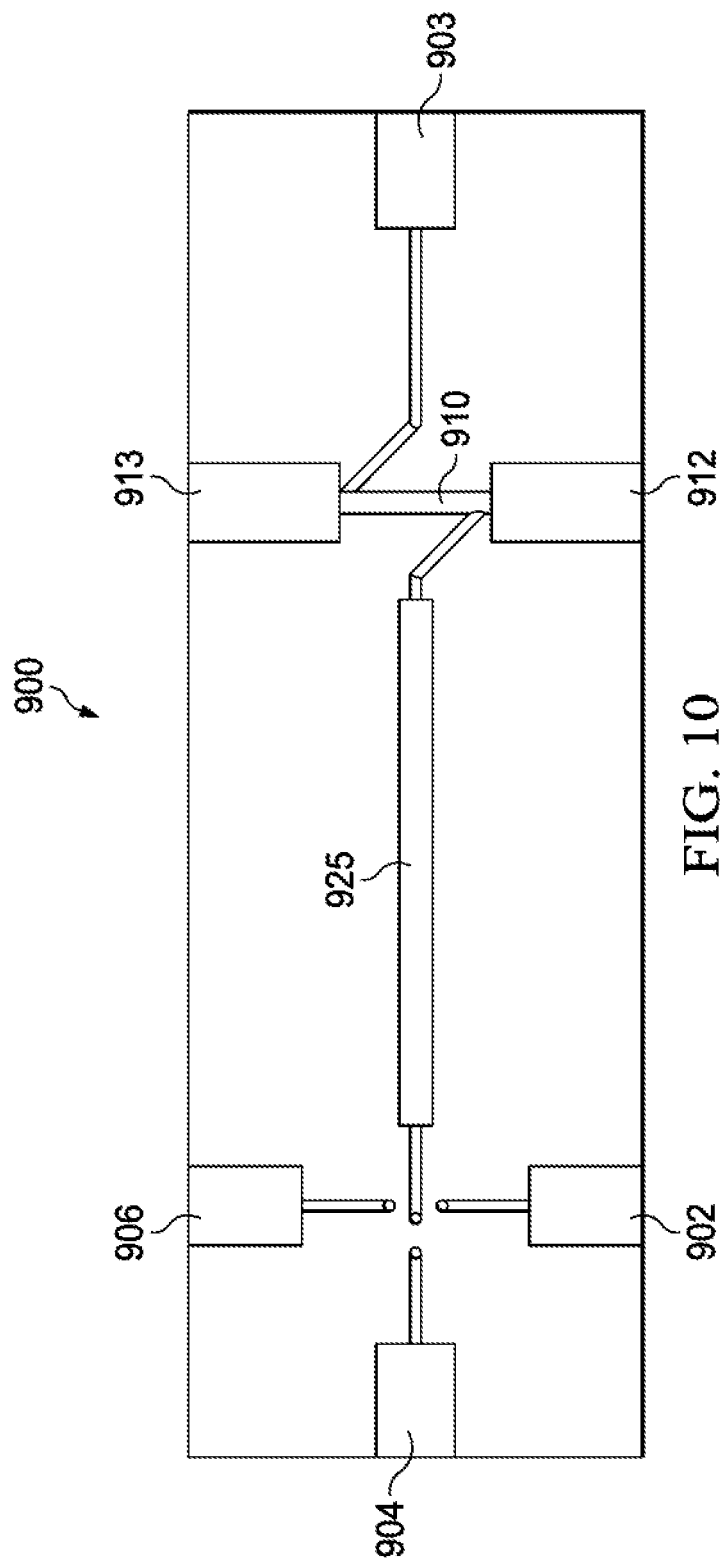
FIG. 10 is a top view of the module of FIG. 9.

Referring now to FIGS. 9 and 10, an alternative embodiment in accordance with the present disclosure is shown. In FIG. 9, a single-use manifold 900 is shown in an isometric view with dotted lines indicating passageways and voids in the body of the manifold 900. As can be seen in FIG. 9, the manifold 900 has openings 912 and 913 proximal one end of the manifold 900. Located between the openings 912 and 913 is a flow cell 910 built into the body of the manifold 900. As described above in connection with the module 1, the openings 912 and 913 can be adapted to provide an ultraviolet (UV) source and detector, respectively (not shown in FIGS. 9 and 10). Located proximal the other end of the body of the manifold 900 are openings 902, 904, and 906. In one particular embodiment, openings 902, 904, and 906 can be adapted to receive tubing and fitting assemblies (not shown) and to receive fluids therethrough once such tubing connections have been made. In addition, openings 908 can be seen on the top surface of the manifold 900. These openings 908 are adapted to be removably connected to corresponding openings of a valve (not shown), such as a rotary valve or rotary shear valve, which can be mounted to the top surface of the manifold 900.

Also shown in FIG. 9 is a column 925 located within the body of the manifold. As shown in FIG. 9, each of the openings 902, 904, and 906 are in fluid communication with a corresponding one of the openings 908. In addition, the column 925 could be in fluid communication with the central opening of the openings 908, as well as the flow cell 910, and the flow cell 910 is also in fluid communication with the opening 903 (which in this particular embodiment can be connected to a waste reservoir, not shown). FIG. 10 is a cross-sectional view of the manifold 900 and also shows the openings 902, 904, 906, and 903, and the fluid communication pathways through the column 925 and flow cell 910, as well as the body of the manifold 900.

Figure 11:
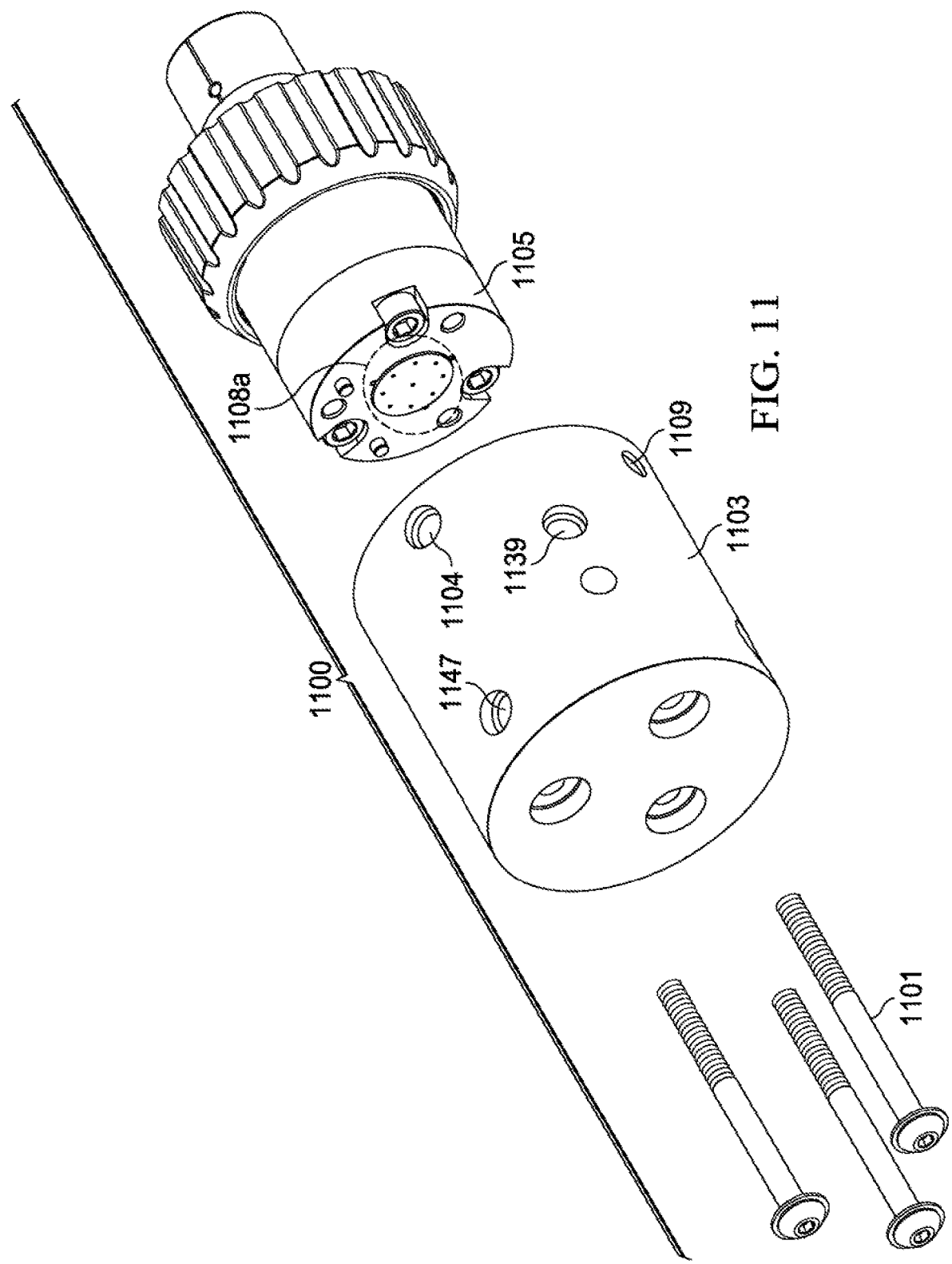
FIG. 11 is an exploded isometric view of a valve assembly 1100 in accordance with one particular embodiment of the present disclosure.
Figure 12:
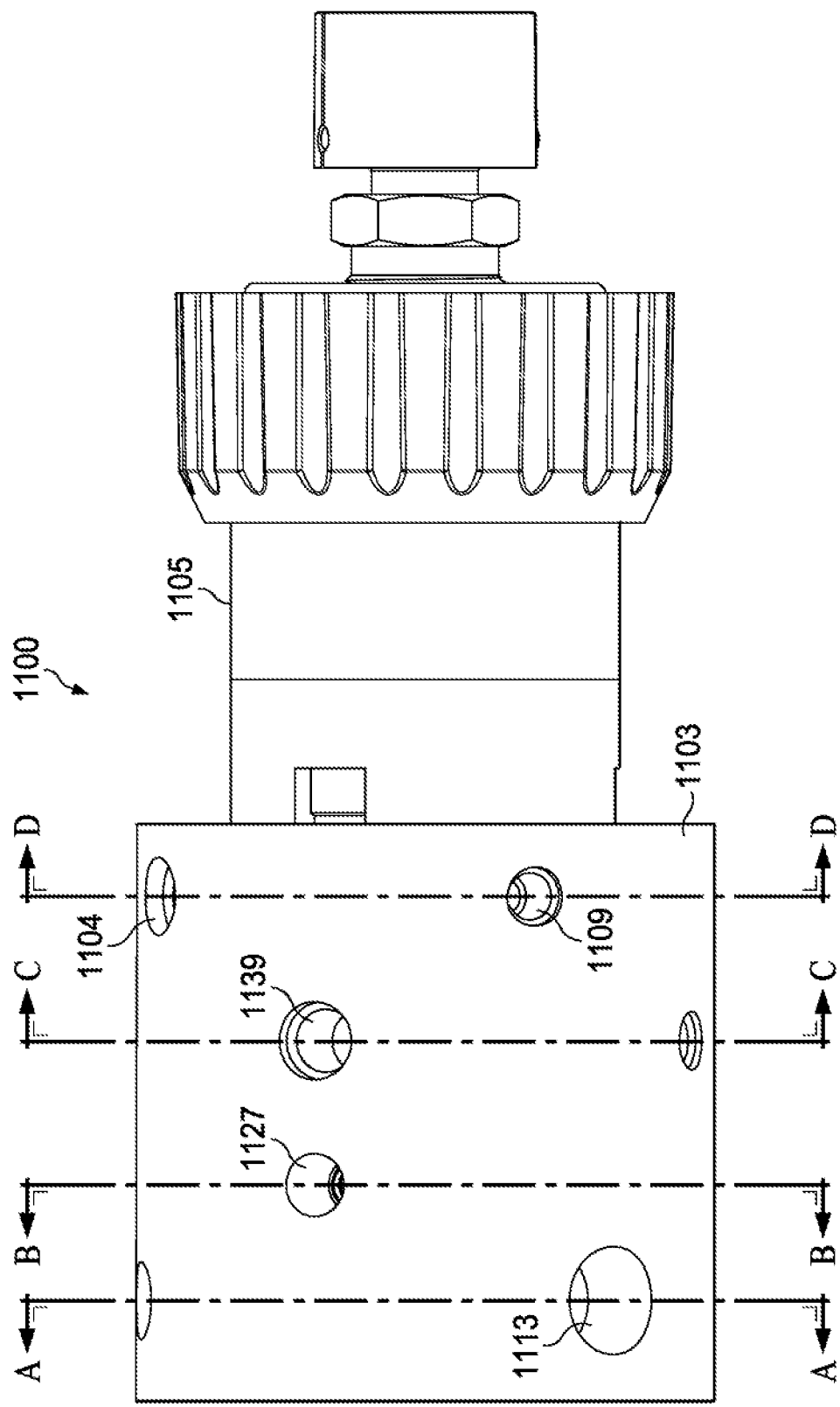
FIG. 12 is a side view of the valve assembly of FIG. 11 in an assembled state.
Figure 13:
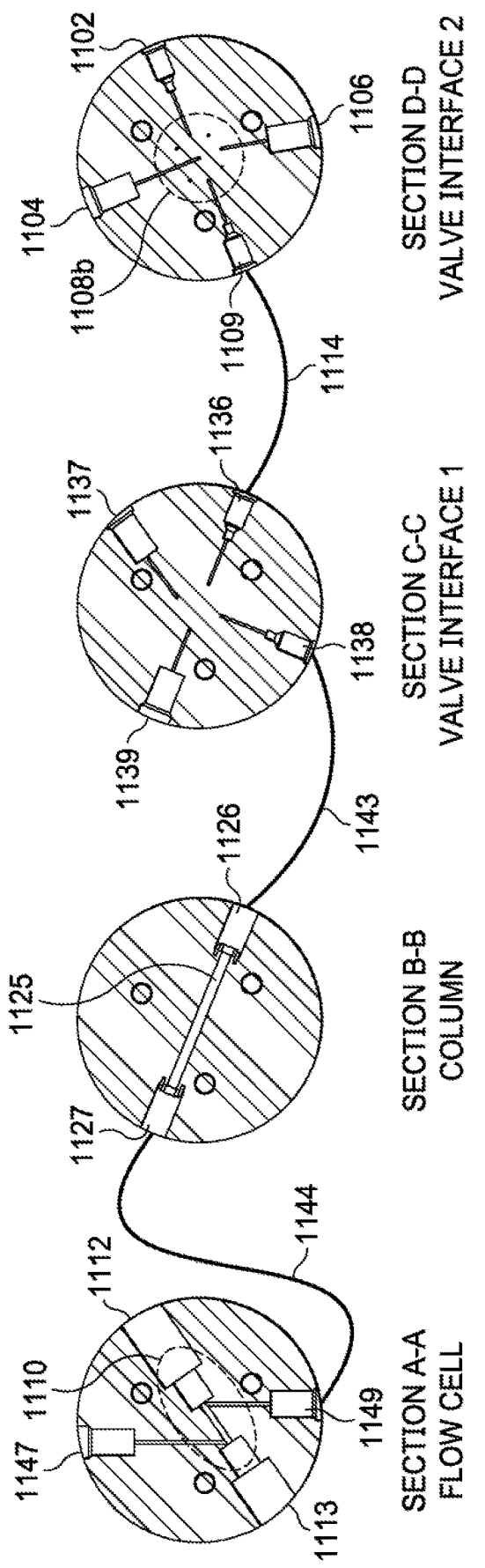
FIG. 13 is a series of cross-sectional views of the manifold 1103 of the valve 1100.

Now referring to FIGS. 11-13, an alternative embodiment of the present disclosure is also illustrated. In FIG. 11, an exploded isometric view of a valve 1100 is provided. The valve assembly 1100 includes an injection valve pod or base 1105, a monolithic or unitary manifold 1103, and three mounting screws 1101. The mounting screws 1101 are adapted to fit into corresponding openings in both the manifold 1103 and the valve pod 1105 to secure the valve 1100 together. The manifold 1103 is generally cylindrical in shape, with one end adapted to have openings each of which corresponds to one of the openings 1108a on the face of the valve pod 1105. Also, shown in FIG. 11 are a plurality of openings in the sides of the manifold 1103. Opening 1147 can be adapted in this particular embodiment to be connected to a waste receptacle, opening 1139 can be adapted to be connected to a waste reservoir, and openings 1109 and 1104 can be adapted to be connected to a sample loop, solvent and/or other fluid sources, such as described below.

In FIG. 12, a side view of the valve assembly 100 in an assembled state is provided. Openings 1113, 1104, 1139, and 1109 in the manifold body 1103 can be as stated before. In addition, opening 1127 is shown. In this particular embodiment, the opening 1127 can be an outlet opening for a column 1125 (as shown in FIG. 13). Also shown in FIG. 12 are lines A-A, B-B, C-C, and D-D.

Now referring to FIG. 13, cross-sectional views of the manifold body 1103 taken along lines A-A, B-B, C-C, and D-D are provided. In this particular embodiment, the manifold body is a single, unitary or monolithic piece. It will be appreciated that the single, monolithic body 1103 can be provided by securely attaching two or more separate pieces together to form the body 1103. It should be appreciated, however, that the manifold body 1103 can comprise two or more separate pieces that are adapted to be removably secured to one another, such that a user can choose to use the same pieces or layers of the manifold 1103 in a different order if desired, or can choose to use more or less pieces for a given application if desired. Thus, the manifold 1103 can be adapted to provide a user with a great deal of flexibility for a wide variety of potential applications.

FIG. 13 also shows potential fluidic connections between and among various openings or ports of the manifold 1103. Starting from the right of FIG. 13 (and it should be appreciated that although right, left, top, bottom, and the like terms of reference are used herein, such references are merely for convenience of the reader with respect to the drawings, and the invention may be embodied in any one of a number of different orientations beyond those shown), section D-D shows a portion of the manifold body 1103 closest to the valve pod 1105 when the valve 1100 is assembled. The layer of the manifold body 1103 shown by section D-D includes, in this one particular illustrative embodiment, a sample inlet 1102, solvent inlets 1104 and 1106, an outlet 1109, as well as openings 1108b.

As also shown in FIG. 13, a sample loop 1114 is connected to outlet 1109 and to inlet 1136 of the portion of the manifold body 1103 shown as section C-C. Section C-C of the manifold body 1103 also includes outlets 1137 and 1139 which can be connected to one or more waste reservoirs, as well as an outlet 1138. Connected to outlet 1138 is a tube 1143. The other end of the sample loop 1143 is connected to an inlet 1126 shown in section B-B. Section B-B further includes column 1125 and an outlet 1127. As also shown in FIG. 13, the outlet 1127 is connected to one end of tubing 1144. The other end of tubing 1144 is connected to inlet 1149 of section A-A. As shown in FIG. 13, section A-A also includes a flow cell 1110, and has a UV source inlet 1112 and a UV detector outlet 1113, as well as outlet 1147. It will be appreciated that tubing (such as tubing 1114, 1143, and 1144) can be securely and removably connected to the various ports on the side of the manifold 1103 to allow fluid communication through the manifold like that described above for module 1.

Those skilled in the art will appreciate that the valve pod 1105 may be made of any of one or more of various materials, including plastics, polymers, and/or metals, or any combination thereof. Those skilled in the art will further appreciate that, for many applications, the materials used for those portions of the pod 1105 which are touched or otherwise may come into contact with a sample may be made of one or more biocompatible materials (such as, for example, polychlorotrifluoroethylene, ultra-high molecular weight polyethylene, polyetheretherketone, etc., or any combination thereof), while other portions of the pod 1105, such as those which do not have surfaces which come into contact with the sample, may be made of other materials, such as steel, aluminum, or the like, and which need not comprise one or more biocompatible materials. Similarly, manifold body 1103 may be made of any one or more materials, such as those noted above, metals (including but not limited to steel and stainless steel), ceramics, and/or an amorphous thermoplastic polyetherimide, such as ULTEM, polyetheretherketone, acrylic, or the like, or a combination thereof. If desired, the manifold 1103 and the valve pod 1105 can be made of the same materials, or can be made of two or more different materials. In addition, while the various features of the manifold 1103 are shown in specific sections in FIG. 13, it will be appreciated that the features may be combined in more or less sections (or layers) of the manifold 1103 than four, and in addition may have a different order than that illustrated in connection with the particular embodiment shown in FIG. 13.

It will be understood and appreciated that, although not shown in FIGS. 7A-7D, 8A-8D, 11, 12, and/or 13, the manifolds illustrated in any or all of such figures may include internal fluid pathways instead of, or in addition to, one or more of the external fluid pathways illustrated. Thus, for example, internal passageways or channels can be provided in any of such manifolds in place of any or all of the external tubing or fluid pathways shown and described.

Figure 14:
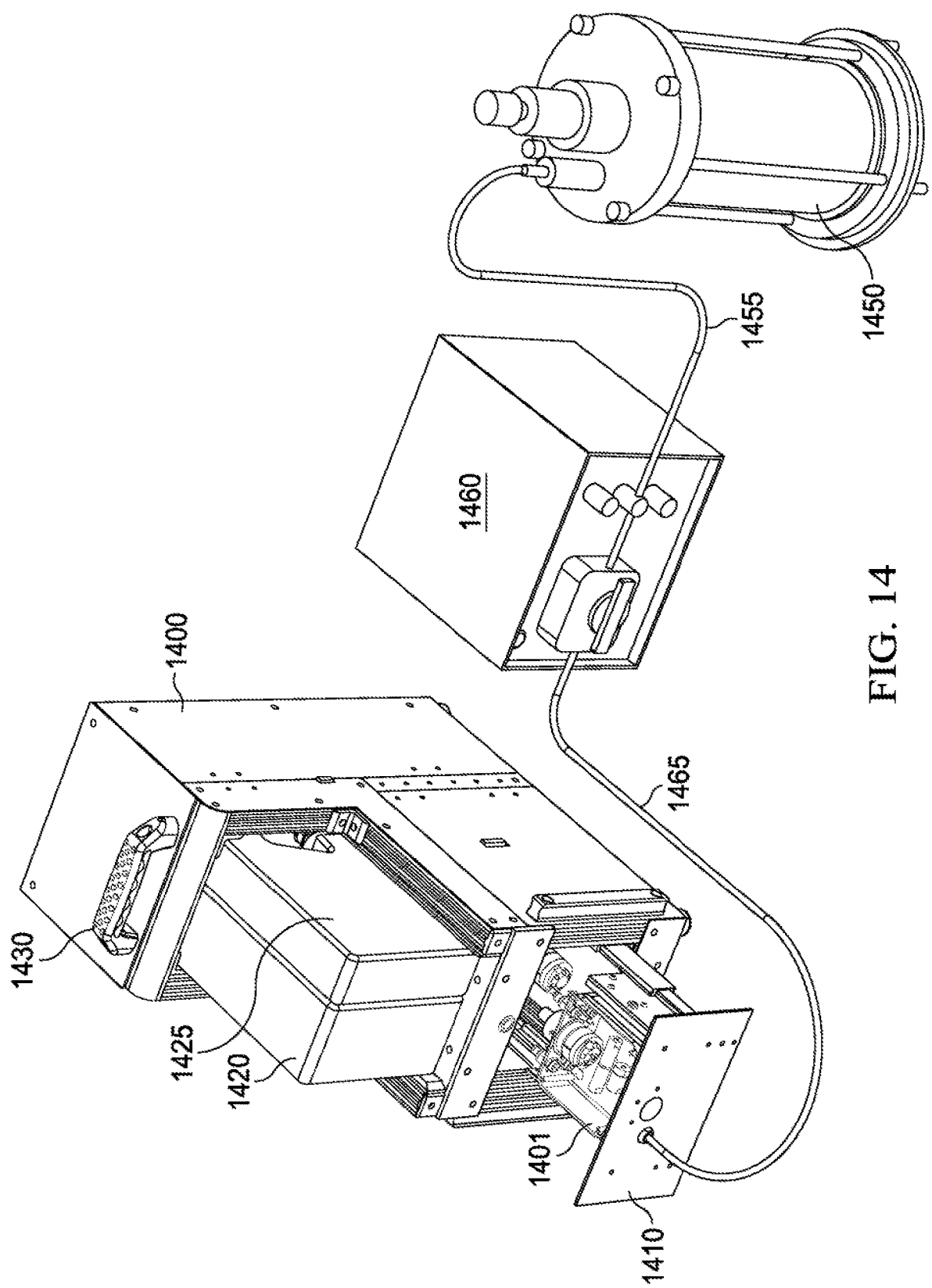
FIG. 14 is an isometric view of one embodiment of a device with a tray for removably receiving a disposable module for use with a bioreactor in accordance with one embodiment of the present disclosure.

Referring now to FIG. 14, a device 1400 in accordance with one embodiment of the present disclosure is shown in an isometric view. The device 1400 as shown in this particular embodiment has two containers 1420 and 1425 which can be removably seated in a first portion of the device 1400. In this embodiment, the device 1400 provides a first portion adapted to removably receive the two containers 1420 and 1425, which can be used to hold, for example, solvents A and B such as described above in connection with the fluid flowpath and its operation as described for various embodiments of the present disclosure. Each of containers 1420 and 1425 can be easily removed and replaced with another container, and can have one or more inlets and outlets (not shown) in either the bottom surface and/or its back surface, any of which can be adapted to allow fluidic communications to other components, such as a disposable module 1401. As shown in FIG. 14, the module 1401 is removably received in a second or seating portion of the device 1400 that is adapted to removably receive the module 1401 in the drawer 1410. The drawer 1410 can be pulled out from or slid into the body of the device 1400 by a user. When the drawer 1410 is pulled out from the main body of the device 1400, the fluidic inlets and outlets of the module 1401 can be easily connected to tubing which can be or is connected to appropriate sources or reservoirs, such as described above with respect to module 1.

It will be appreciated that, in the particular embodiment shown in FIG. 14, solvent container 1420 is larger than solvent container 1425. In one particular embodiment, solvent container 1420 may be a two-liter container, with solvent container 1425 a one-liter container. Those skilled in the art will appreciate, however, that the solvent containers 1420 and 1425 may be the same size, and that the device 1400 may be adapted to have just one solvent container, or possibly more than two solvent containers, if so desired for one or more particular applications or uses. Although not shown in FIG. 14, it should be appreciated that the device 1400 can provide holes or openings in the first portion which are adapted to receive and cooperate with corresponding portions of the bottom surfaces of the solvent containers 1420 and 1425. Such openings can be used to allow easier fluidic connections between openings or outlet ports located on the bottom surfaces of the solvent containers 1420 and 1425 and appropriate tubing leading to inlet ports of the module 1401 when the module 1401 is located in the drawer 1410.

Although solvent containers 1420 and 1425 as illustrated in FIG. 14 sit atop a surface portion of the device 1400 adapted to removably receive them, and are illustrated as semi-rigid containers, such as might be made of plastic, the device 1400 can be adapted to removably receive other types of solvent containers and can be adapted to removably receive such solvent containers in other locations. For example, the device 1400 can be adapted to removably receive and hold one or more solvent containers that comprise a flexible bag that may hold one or more fluids therein, or may comprise a flexible bag located within a rigid or semi-rigid box (e.g., such as made of cardboard, plastic, or the like). Moreover, the device 1400 may be adapted to removably receive and hold one or more solvent containers wholly or partially within the device 1400.

Although not shown in FIG. 14, it will be understood and appreciated that the device 1400 may include additional components, such as valves, sensors, and connections like those described above and illustrated for the fluid engine 3. In addition, the device 1400 may further include, coupled to a fluid engine 3 or the like, a processor, memory, and computer software instructions, as well as connections to a UV source and detector which can be connected to the flow cell of the module 1401. The device 1400 thus may comprise a control system (not shown) which may include a fluid engine like fluid engine 3 or a portion thereof, as well as a computer processor, memory (volatile and non-volatile memory), and instructions (such as in the form of executable computer software stored in memory) for operation of the control system by execution on the processor, together with operation of the module 1401, for receiving data from the flow cell (e.g., via the UV source and detector when connected to the appropriate openings of the flow cell of the module 1401), and/or for storing, analyzing, displaying, and/or outputting such data. Although not shown in FIG. 14, it will be appreciated that the device 1400 may further include a compartment or other portion adapted to receive and hold one or more batteries, which can be coupled to the computer processor, memory, and/or fluid engine 3 or other electronics, such that the device 1400 may be used without an external power source. Alternatively, the device 1400 may further include a socket, cord or other connection to allow the electronics (e.g., the computer processor, memory, and control systems) of the device 1400 to be connected to an external power source. The device 1400 may be further adapted to allow a user to switch between an external power source and one or more batteries connected to the device

1400. In addition, or alternatively, the device 1400 may contain rechargeable batteries, which can supply power when charged and/or when the device 1400 is not connected to an external power source.

In one embodiment of the present disclosure, the solvents and reagents to be used may be included in one or more pre-packaged forms, and the solvent containers and/or packaging may contain one or more identifiers. For example, the package with solvents and/or reagents therein may include any one or more of following types of identifiers: a RFID tag, a barcode, a chip or smart card, a magnetic strip, or the like or a combination thereof. In such an embodiment, the device 1400 may include one or more appropriate readers (e.g., a magnetic card reader for a magnetic strip, a barcode reader for a bar code, a smart chip reader for a smart chip, and/or an RFID reader for an RFID tag) for the one or more identifiers used. In some cases, different solvent or reagent packages may use different identifiers, and so the device 1400 may be provided with a number of readers. The readers may be located proximal or adjacent to where the identifier is anticipated to be located when the solvent or reagent container or package is attached to the device 1400. Such identifiers may contain information as the particular solvent or reagent package or container that is attached to the device 1400, the particular solvents, reagents, amounts contained therein, etc., which may be used by the control system of the device 1400, which may be programmed to read and use such information. Similarly, the module 1401 may contain an identifier such as any one or more of those described above, and the device 1400 may include one or more readers such as any one or more of those described above and located in, proximal or adjacent the drawer 1410 or other location in which the module 1401 may be removably located, in which case the control system of the device 1400 may be programmed to check the reader to see if any identifier of a module 1401 has been found, and if so, to obtain information from the reader (such as information identifying the module 1401, the column included therein, the guard column included therein, whether or not the module 1401 is biocompatible, a pressure range of operability, and the like), and then use such information. For example, the control system might use such information to check to be sure that the appropriate module 1401 and solvents/reagents are used for a particular sample and to provide a warning if that is not the case.

In some embodiments, the device 1400 may be subject to remote control of its operations, such as by a wired or wireless connection. For example, a user may use a remote control attached by a wired connection (not shown) to an input data port of the device 1400, with the user able to control the operation of the device 1400. The wired connection further can be removable, such as a socket connection, a USB connection, or other data connection. Alternatively, the device 1400 can include a wireless transmitter and/or receiver so that a user can remotely operate the device 1400 from a wireless control device, which may be a smartphone, tablet, computer, or other device. Moreover, the device 1400 can include software to allow the device to respond to requests for information provided remotely and transmit data from the device 1400 to a remote location. Such data transmissions may be by wired or wireless connection, and the receiving device may be a smartphone, tablet, computer, or other device that may be programmed to send a request for information and then receive the requested information from the device 1400.

In FIG. 14, a bioreactor vessel 1450 is also shown. As indicated for this particular embodiment, tubing 1455 connects the bioreactor 1450 with a sampling system 1460. For purposes of the present disclosure, the sampling system 1460 may be a conventional system, such as one of the Seg-Flow sampling system models commercially available from Flownamics of Madison, Wis. As also shown, tubing 1465 connects the sampling system 1460 to an input of the module 1401 via an opening in the front face of the drawer 1410 of device 1400. As discussed above in the present disclosure, those skilled in the art will appreciate that the sampling system 1460 and the module 1401 can be connected to a common control system which can be programmed to automatically obtain samples from the bioreactor 1450, such as at predetermined time intervals, provide the samples to the module 1401, and analyze the samples with the module 1401 and/or with additional instrumentation (such as if the module 1401 includes a flow cell that does not include a UV source and/or a UV detector).

It should be appreciated that one advantage of the particular configuration shown in FIG. 14 is that it helps automate the collection and transmission of samples from the bioreactor 1450 to the module 1401 in a way that ensures that the samples from the bioreactor 1450 are not contaminated during collection, sampling, and/or testing, and also ensures that the sampling process does not contaminate the contents of the bioreactor 1450. In addition, the control system of device 1400 as described above can also be connected to the sampling system 1460, and can be used to control the operation of the sampling system 1460 together with that of the device 1400 and the module 1401. It should be noted that, although not shown, the sampling system 1460 and its components may be combined into the device 1400 and so, instead of two separate items connected by tubing or another fluid pathway, the device 1400 might instead include the components of the sampling system 1460 and such components of the sampling system can be controlled by the control system of the device 1400.

In FIG. 14, the top of the module 1401 is shown as removed for illustration purposes only. As discussed above, the module 1401 may have a removable top or other side, but also may be designed so that it is not easily opened and/or may be provided with tamper-resistant sides.

The device 1400 also includes a handle 1430 on a top side thereof. In one particular embodiment, the device 1400 can be made of various plastics and/or metals, or combinations thereof, and may weigh anywhere from approximately 5 Kilograms to 20 Kilograms or more (without full solvent containers 1420 and 1425). If the solvent containers 1420 and 1425 are full, and a module 1401 is included and seated in the drawer 1410, the weight of the device 1400 can be expected to be from about 2.5 Kilograms to about 22 Kilograms. In one particular embodiment, the device 1400 can measure about eighteen inches by eighteen inches by twelve inches. It will be appreciated, however, that the device may be even smaller and weigh even less, such as a device 1400 that measures about nine by nine by six inches and weighs no more than ten Kilograms. Thus, it will be appreciated that the device 1400 can be relatively small, easy to move, and thus is portable, even with solvents included in the solvent containers 1420 and 1430. The size, portability and ease of movement of the device 1400 means that, in addition to its convenient use and portability in laboratory and industrial manufacturing facilities, the device 1400 can be used "in the field." For example, the device 1400 can be used with a module 1401 to test a well, a lake, pond or stream, an oasis in a desert, a water tank in a jungle village, and so forth, such as may be desirable for environmental analyses. Moreover, the use of the device 1400 and/or module 1401 can be used to test for a wide variety of characteristics and/or a variety of sample sources, such as the presence or absence of certain things, including but not limited to suspected contaminants, microorganisms, proteins, and the like. Moreover, the portability of the device 1400, together with its ease of use with a variety of modules 1401 which can be designed to analyze varying samples for varying characteristics, means that hospitals, medical clinics, and the like in remote locations can be provided with the ability for on-site sampling, testing, and analysis, such as for disease analysis by osmosis.

Figure 15A:
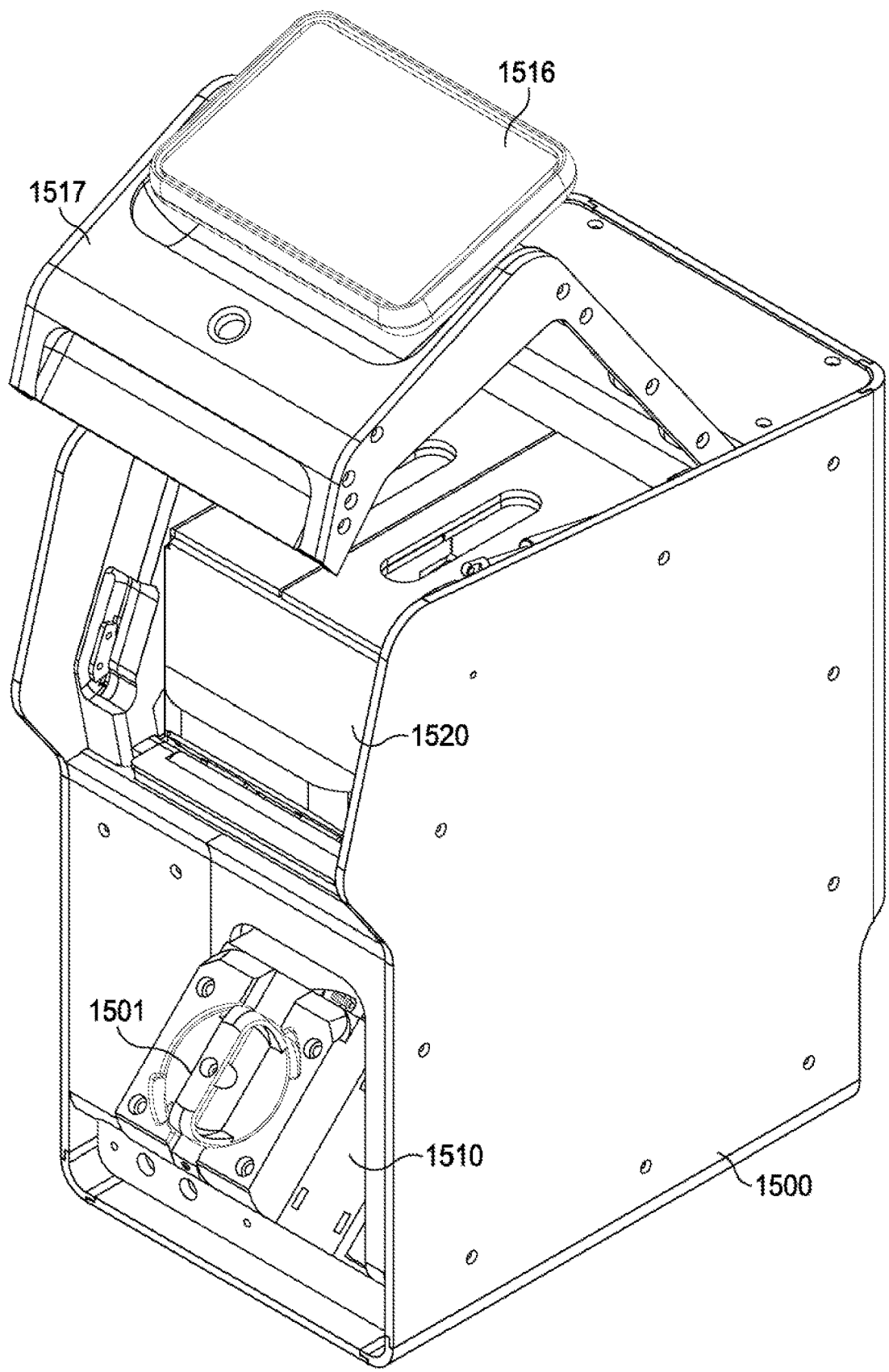
FIGS. 15A and 15B are views of a portable device with a hinged nest for receiving a disposable module and a top portion for receiving one or more fluid containers in a first position (with the hinged nest and the top portion shown in an open position) and in a second position (with the top portion in a closed position and the hinged nest still in an open position), respectively.
Figure 15B:
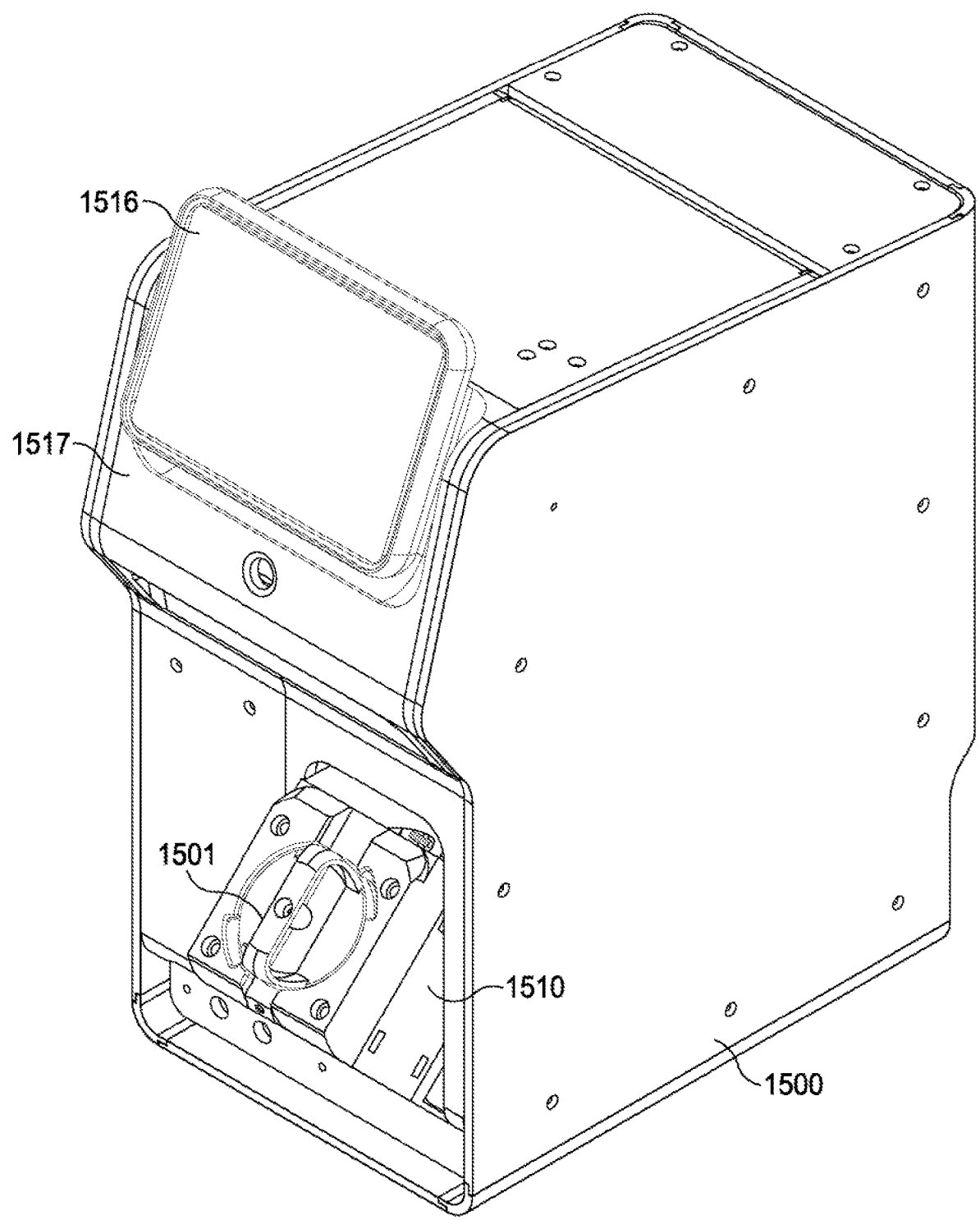

In one or more embodiments of the present disclosure, a module may be adapted to be removably secured in a nest of a portable device. The nest may be hinged and may be adapted to removably receive the module therein. The module may be disposable so that it is used for one particular application, then removed from the device and, when the device is used next, a similar or different module may be used for the next intended application of the device. In FIG. 15A, a device 1500 is shown. The device 1500 may be like device 1400 as described above, and may have a handle (not shown), and may have a surface area or top portion adapted to removably receive one or more fluid containers, such as solvent or reagent container 1520 as illustrated in FIG. 15A. As also shown in FIG. 15A, the top portion of the device 1500 for the container 1520 may also have a movable cover 1517 that may be hinged or otherwise movable or swingable from a first, closed position, to a second, open position. In FIG. 15A, the cover 1517 is shown in the second, open position. With the cover 1517 in the open position, a user can easily place a container 1520 into place in the top portion of the device 1500, or can remove a container 1520 from the top portion. In this particular example shown in FIG. 15A, a display 1516 is mounted to the cover 1517. The display 1516 can be connected to one or more appropriate control systems (such as any of those described elsewhere herein) and can be used to display data or to input data or commands (such as if the display 1516 comprises a touch screen panel or a tablet computer). In FIG. 15B, the cover 1517 is shown in a closed position. The device 1500 may also have a hinged nest 1510 adapted to removably receive and hold a disposable module 1501. As shown in FIGS. 15A and 15B, the hinged nest 1510 is in an open position and a disposable module 1501 is seated within a space therefor in the hinged nest 1510.

It will be appreciated that, in the particular embodiment shown in FIG. 15A, a single solvent container 1520 is shown. The container 1520 may have two or more separate reagent containers therein, such as two or more flexible bags containing reagents. If desired, the containers within container 1520 may be the same size or may be different sizes. Further, the device 1500 may be adapted to have just one solvent container, or possibly more than two solvent containers, if so desired for one or more particular applications or uses. Although not shown in FIG. 15A, it should be appreciated that the device 1500 can provide holes or openings in the first portion which are adapted to receive and cooperate with corresponding portions of the bottom surfaces of the solvent container 1520. Such openings can be used to allow easier fluidic connections between openings or outlet ports located on the bottom surface of the solvent container 1520 and appropriate tubing leading to inlet ports of the module 1501 when the module 1501 is located in the nest 1510.

Although solvent container 1520 as illustrated in FIG. 15A sits atop a surface portion of the device 1500 adapted to removably receive it, and is illustrated as a semi-rigid container, such as might be made of plastic, the device 1500 can be adapted to removably receive other types of solvent containers and can be adapted to removably receive such solvent containers in other locations. For example, the device 1500 can be adapted to removably receive and hold one or more solvent containers that comprise a flexible bag that may hold one or more fluids therein, in addition to or in lieu of one or more flexible bags located within a rigid or semi-rigid box (e.g., such as made of cardboard, plastic, or the like). Moreover, the device 1500 may be adapted to removably receive and hold one or more solvent containers wholly or partially within the device 1500.

In one embodiment of the present disclosure, the solvents and reagents to be used may be included in one or more pre-packaged forms, and the solvent containers and/or packaging may contain one or more identifiers. For example, the package with solvents and/or reagents therein may include any one or more of following types of identifiers: a RFID tag, a barcode, a chip or smart card, a magnetic strip, or the like or a combination thereof. In such an embodiment, the device 1500 may include one or more appropriate readers (e.g., a magnetic card reader for a magnetic strip, a barcode reader for a bar code, a smart chip reader for a smart chip, and/or an RFID reader for an RFID tag) for the one or more identifiers used. In some cases, different solvent or reagent packages may use different identifiers, and so the device 1500 may be provided with a number of readers. The readers may be located proximal or adjacent to where the identifier is anticipated to be located when the solvent or reagent container or package is attached to the device 1500. Such identifiers may contain information as the particular solvent or reagent package or container that is attached to the device 1500, the particular solvents, reagents, amounts contained therein, etc., which may be used by the control system of the device 1500, which may be programmed to read and use such information. Similarly, the module 1501 may contain an identifier such as any one or more of those described above, and the device 1500 may include one or more readers such as any one or more of those described above and located in, proximal or adjacent the hinged nest 1510 or other location in which the module 1501 may be removably located, in which case the control system of the device 1500 may be programmed to check the reader to see if any identifier of a module 1501 has been found, and if so, to obtain information from the reader (such as information identifying the module 1501, the column included therein, the guard column included therein, whether or not the module 1501 is biocompatible, a pressure range of operability, and the like), and then use such information. For example, the control system might use such information to check to be sure that the appropriate module 1501 and solvents/reagents are used for a particular sample and to provide a warning if that is not the case.

In some embodiments, some or all of the operations of the device 1500 may be subject to remote control, such as by a wired or wireless connection. For example, a user may use a remote control attached by a wired connection (not shown) to an input data port of the device 1500, with the user able to control the operation of the device 1500. The wired connection further can be removable, such as a socket connection, a USB connection, or other data connection. Alternatively, the device 1500 can include a wireless transmitter and/or receiver so that a user can remotely operate the device 1500 from a wireless control device, which may be a smartphone, tablet, computer, or other device. Moreover, the device 1500 can include software to allow the device to respond to requests for information provided remotely and transmit data from the device 1500 to a remote location. Such data transmissions may be by wired or wireless connection, and the receiving device may be a smartphone, tablet, computer, or other device that may be programmed to send a request for information and then receive the requested information from the device 1500. The receiving device in such cases may also be operable with software to transmit data and control information to the device 1500, such that an operator may remotely monitor operations of the device and data therefrom and may provide instructions or controls to the device 1500 from a remote location.

Although not shown in FIG. 15A or 15B, the device 1500 may include additional components, such as valves, sensors, and connections like those described above and illustrated for the fluid engine 3. In addition, the device 1500 may further include, coupled to a fluid engine 3 or the like, a processor, memory, and computer software instructions, as well as connections to a UV source and detector which can be connected to a flow cell of the module 1501. The device 1500 thus may comprise a control system (not shown) which may include a fluid engine like fluid engine 3 or a portion thereof, as well as a computer processor, memory, and instructions for operation of the control system together with operation of the module 1501, for receiving data from the flow cell (e.g., via the UV source and detector when connected to the appropriate openings of the flow cell of the module 1501), and/or for storing, analyzing, displaying, and/or outputting such data.

Although not shown in FIG. 15A or 15B, the device 1500 may be connected to a sampling system and/or a bioreactor vessel, such as described above with respect to device 1400, and may be used as described above with respect to device 1400. In addition, the device 1500 may incorporate the components of the sampling system 1460 shown in FIG. 14 and described above if desired, thus allowing the device 1500 to control the sampling from a bioreactor or other source (not shown in FIG. 15A or 15B).

In one particular embodiment, the device 1500 can be made of various plastics and/or metals, or combinations thereof, and may weigh anywhere from approximately 0.3 Kilograms to 20 Kilograms or more (without full solvent container 1520). If the solvent container 1520 is full, and a module 1501 or 2201 is included and seated in the device 1500, the weight of the device 1500 can be expected to be from about 2.5 Kilograms to about 22 Kilograms. In one particular embodiment, the device 1500 can measure about eighteen inches by eighteen inches by twelve inches. It will be appreciated, however, that the device may be even smaller and weigh even less, such as a device 1500 that measures about nine by nine by six inches and weighs no more than ten Kilograms. Thus, it will be appreciated that the device 1500 can be relatively small, easy to move, and thus is portable, even with solvents included in the solvent containers 1520 and 1530. The size, portability and ease of movement of the device 1500 means that, in addition to its convenient use and portability in laboratory and industrial manufacturing facilities, the device 1500 can be used "in the field." For example, the device 1500 can be used with a module 1501 or 2201 to test a well, a lake, pond or stream, an oasis in a desert, a water tank in a jungle village, and so forth, such as may be desirable for environmental analyses. Moreover, the use of the device 1500 and/or module 1501 or 2201 can be used to test for a wide variety of characteristics and/or a variety of sample sources, such as the presence or absence of certain things, including but not limited to suspected contaminants, microorganisms, proteins, and the like. Moreover, the portability of the device 1500, together with its ease of use with a variety of modules 1501 or 2201 which can be designed to analyze varying samples for varying characteristics, means that hospitals, medical clinics, and the like in remote locations can be provided with the ability for on-site sampling, testing, and analysis, such as for disease analysis by osmosis.

Figure 16:
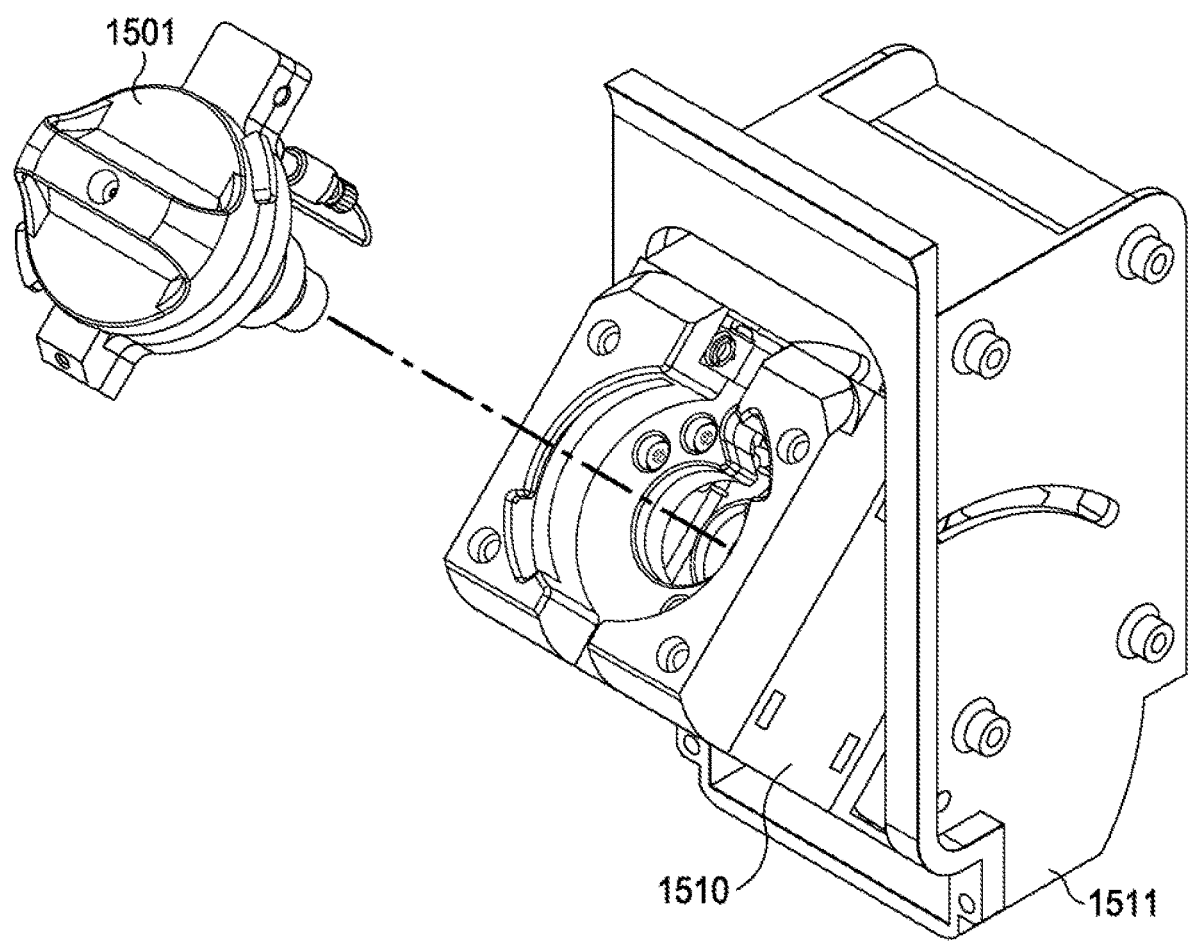
FIG. 16 is an enlarged, exploded view of the hinged nest and module of FIG. 15.
Figure 17:
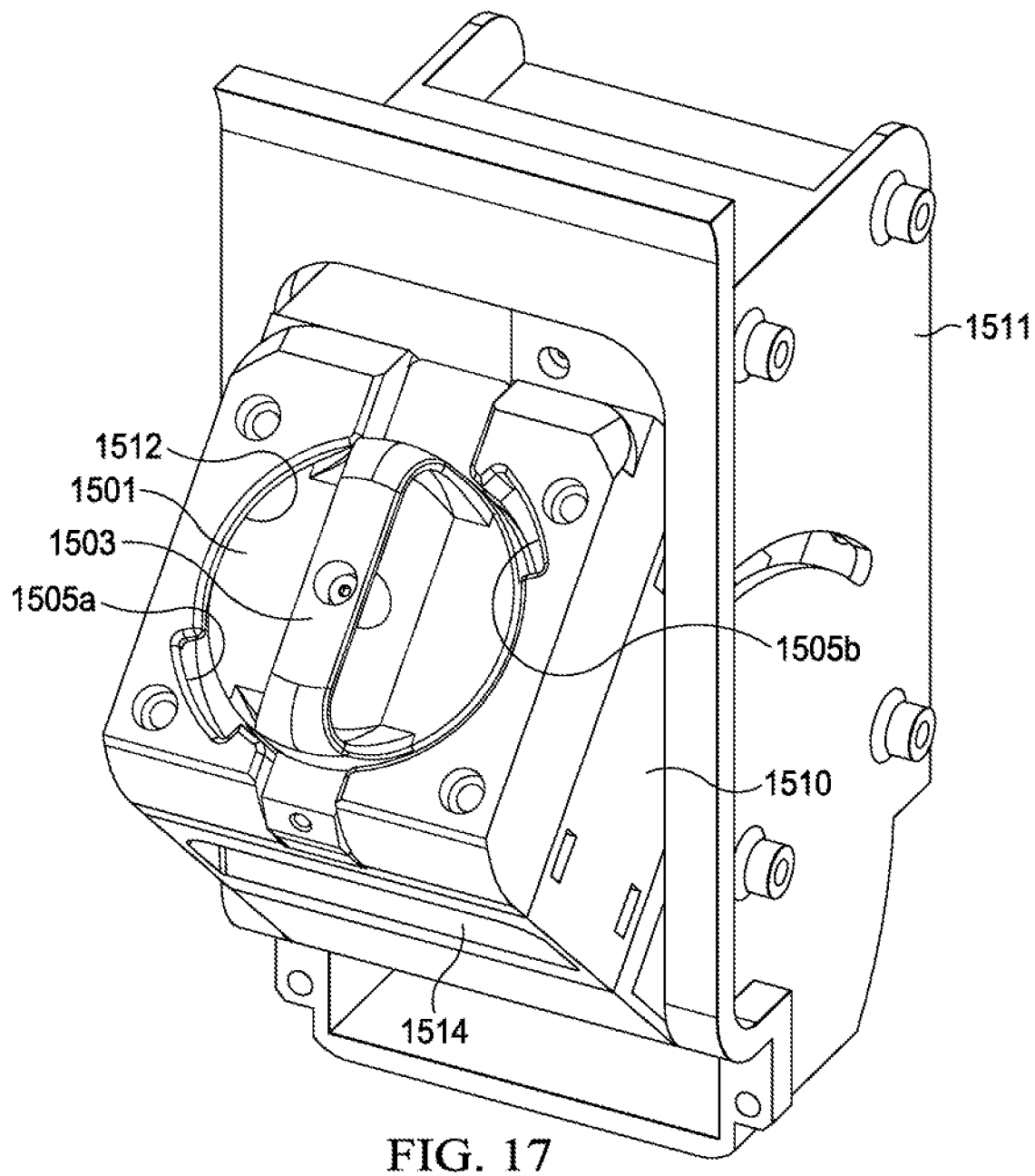
FIG. 17 is an enlarged view of the hinged nest and module in an assembled state with the hinged nest in an open position.

Referring now to FIG. 16, an enlarged view of the disposable module 1501 and the hinged nest 1510 of the device 1500 is provided. For simplicity and ease of reference, the device 1500 is not shown in FIGS. 16 and 17 except for the hinged nest 1510 and the holder 1511. Similarly, like items and features have the same numbers ascribed to them in the various Figures for convenience. As illustrated in FIG. 17, the holder 1511 can be attached to the device 1500 so that the holder 1511 is located internally within the device 1500 and so that the hinged nest 1510, when in a closed position, does not extend from the surface of the hinged nest 1510, which in turn can be flush with the surface of the device 1500. As illustrated in FIGS. 15 and 16 (as well as additional Figures as discussed below), the nest 1510 is hinged at the bottom thereof and the top portion thereof swings outwardly from the exterior surface of the device 1500.

Figure 18:
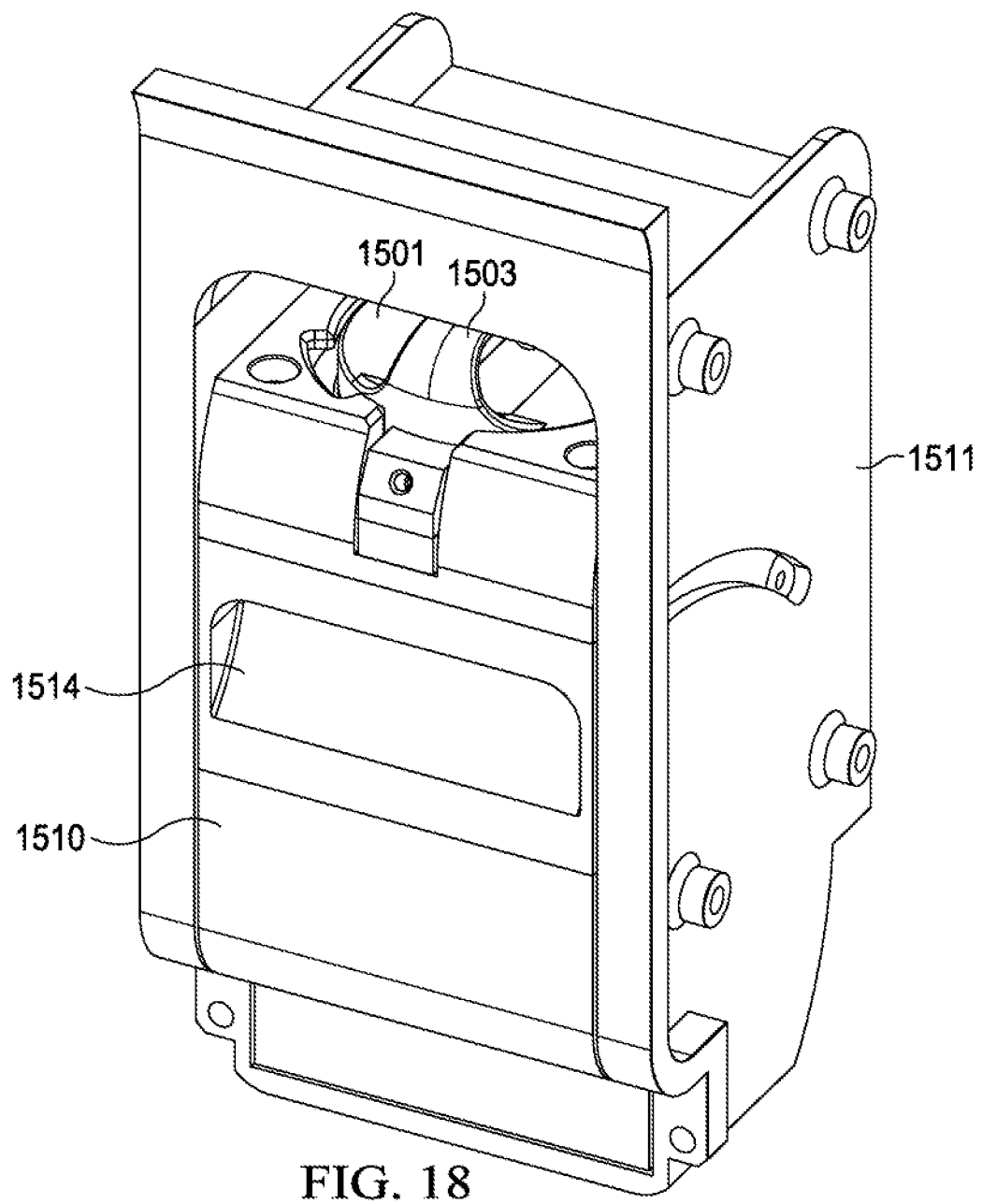
FIG. 18 is an enlarged view of the hinged nest and module in an assembled state with the hinged nest in a closed position.

In FIG. 17, a detailed view of the module 1501 and the hinged nest 1510 is provided, with the nest 1510 in an open position and with a module 1501 received by and held within a nest portion 1512 of the nest 1510. An enlarged view of the hinged nest 1510 with a module 1501 held therein in a closed position is provided in FIG. 18. As shown in FIG. 17, the nest 1510 may further include a circular nest portion 1512 which is adapted to removably receive and hold the module 1501 therein. In addition, the hinged nest 1510 may include notches or open portions 1505a and 1505b which are adapted to removably receive and hold corresponding projections of the module 1501. The module 1501 may have a handle 1503 centrally located and extending from the top portion thereof. The handle 1503 allows a user to more easily grasp and turn the module 1501 to tighten it or loosen it in the nest 1512 as desired. The front face of the hinged nest 1510 as shown in FIG. 17 may further include an internal handle portion 1514 to allow a user to easily grip the hinged nest 1510 and push or pull on it to close or open it as desired.

Figure 19:
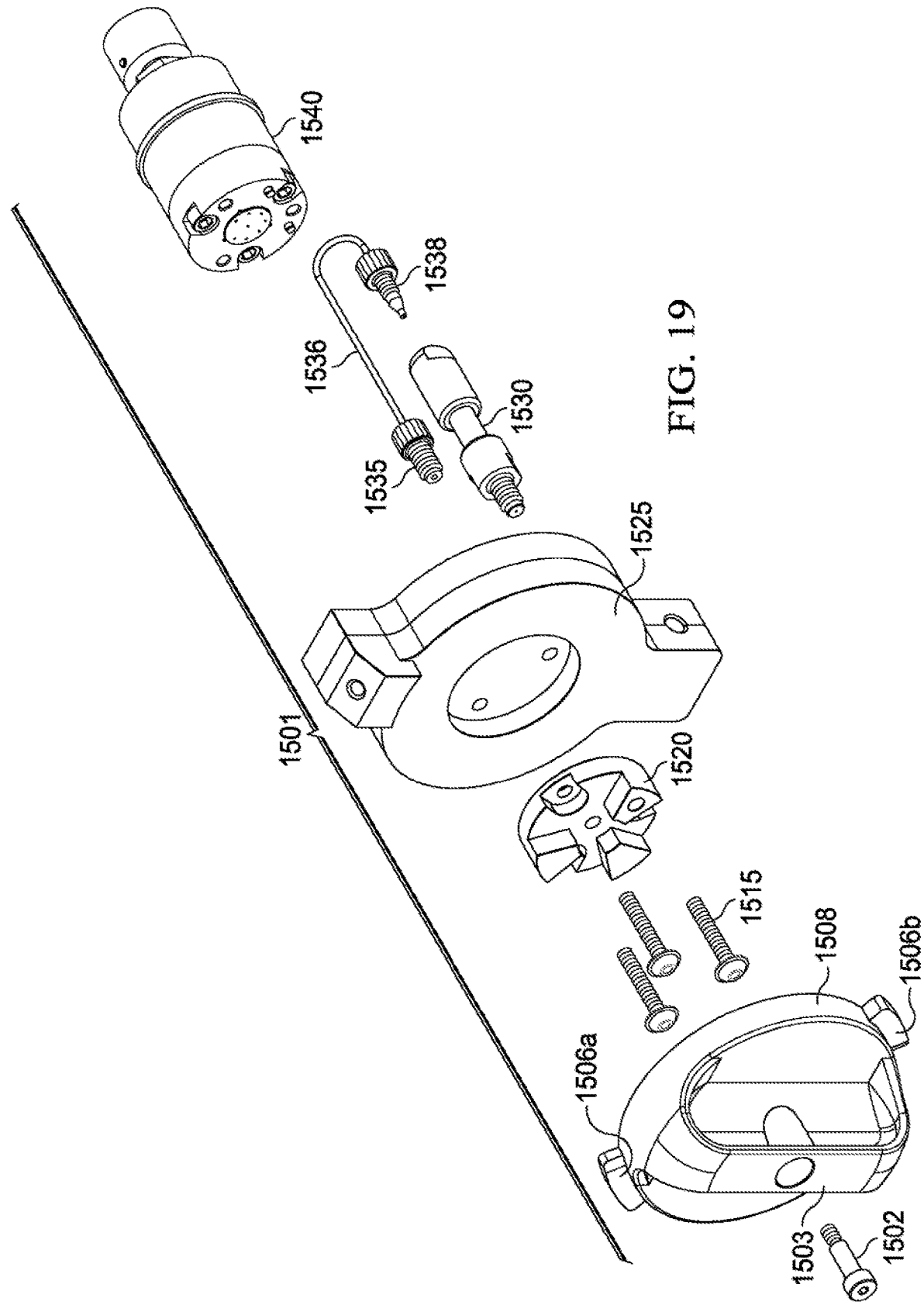
FIG. 19 is an exploded view of a module in accordance with one embodiment of the present disclosure.

Now referring to FIG. 19, an exploded view of a module 1501 in accordance with the present disclosure is provided. The module 1501 may comprise a top 1508, a handle mount 1520, a manifold 1525, a column 1530, a guard column 1535, and a valve 1540. A screw 1502 may be used to securely fasten the module top 1508 to the handle mount 1520. In addition, screws 1515 may be used to securely fasten the handle mount 1520, the manifold 1525, and the valve 1540 together. The guard column 1535 can be attached by tubing 1536 and a fitting assembly 1538 to an end of the column 1530. It should be noted that the guard column 1535 and the column 1530 may be selected for a particular module 1501 that, in turn, is intended for use in a particular application, such as may involve higher or lower pressures, one or more solvents with different chemical properties, one or more types of samples, and so forth. The top 1508 of the module 1501 also includes two opposing projections 1506a and 1506b. These projections 1506a, 1506b are adapted to cooperate with and removably fit in the notches 1505a, 1505b of the nest 1510. As indicated by the threaded end portions of the guard column 1535 and the column 1530, these ends may be removably and securely attached to the back side of the manifold 1525 by screwing the threaded end portions of the guard column 1535 and/or column 1530 into corresponding openings in the back side of the manifold 1525 with internal threads adapted to removably receive and securely hold such end portions The module 1501 may be inserted into the nest 1510 such that the projections 1506*a* and 1506*b* are aligned with openings 1505*a* and 1505*b*, respectively. A helical groove (not shown), similar to threading for a screw, may be provided by and within the nest 1510. As the handle and the module 1501 is rotated, the projections 1506*a* and 1506*b* travel along the helical groove provided by the nest 1510. As the projections 1506*a* and 1506*b* move along the helical groove, the module 1501 moves into a slightly lower position in the nest 1510 relative to the exterior surface of the nest 1510, thereby securing the module 1501 into position in the nest. To remove the module 1501 from the nest 1510, an operator or user may similarly rotate the handle in the opposite direction, which will cause the projections 1506*a* and 1506*b* to reverse their paths along the helical groove until the module 1501 can be removed from the nest 1510.

A plurality of fluid connections may be made with the module 1501 in a variety of ways. For example, conventional tubing and fitting assemblies may be used to securely and removably connect tubing into ports 1521*a*, 1521*b*, 1521*e*, and 1521*f* in the manifold. In another alternative example, the male end of one or more biased fitting assemblies may be threaded into any one or more of ports 1521*a*, 1521*b*, 1521*e*, and 1521*f* in the manifold. In this particular embodiment (not shown), the nest 1510 may be provided with corresponding spring-loaded female fitting assemblies, each of which is adapted to receive and removably hold a male-shaped biased fitting assembly. When the handle is rotated, the resulting lowering of the module 1501 into the nest 1510 couples these fittings together to provide appropriate sealing connections. Spring-loaded fitting assemblies that may be used for this example include those shown and described in co-pending U.S. patent application Ser. No. 15/617,792, filed on Jun. 8, 2017, and published on Sep. 28, 2017, as U.S. Patent Application Publication No. 2017/0276275, which is hereby incorporated by reference herein. In addition, it should be noted that the module 1501 (as well as the other modules, devices, and configurations thereof as described and shown in the present disclosure, including without limitation module 2201 and/or a manifold and valve combination) may be incorporated into or comprise an analytical instrument system, such as a gas or liquid chromatography system.

Figure 20A:
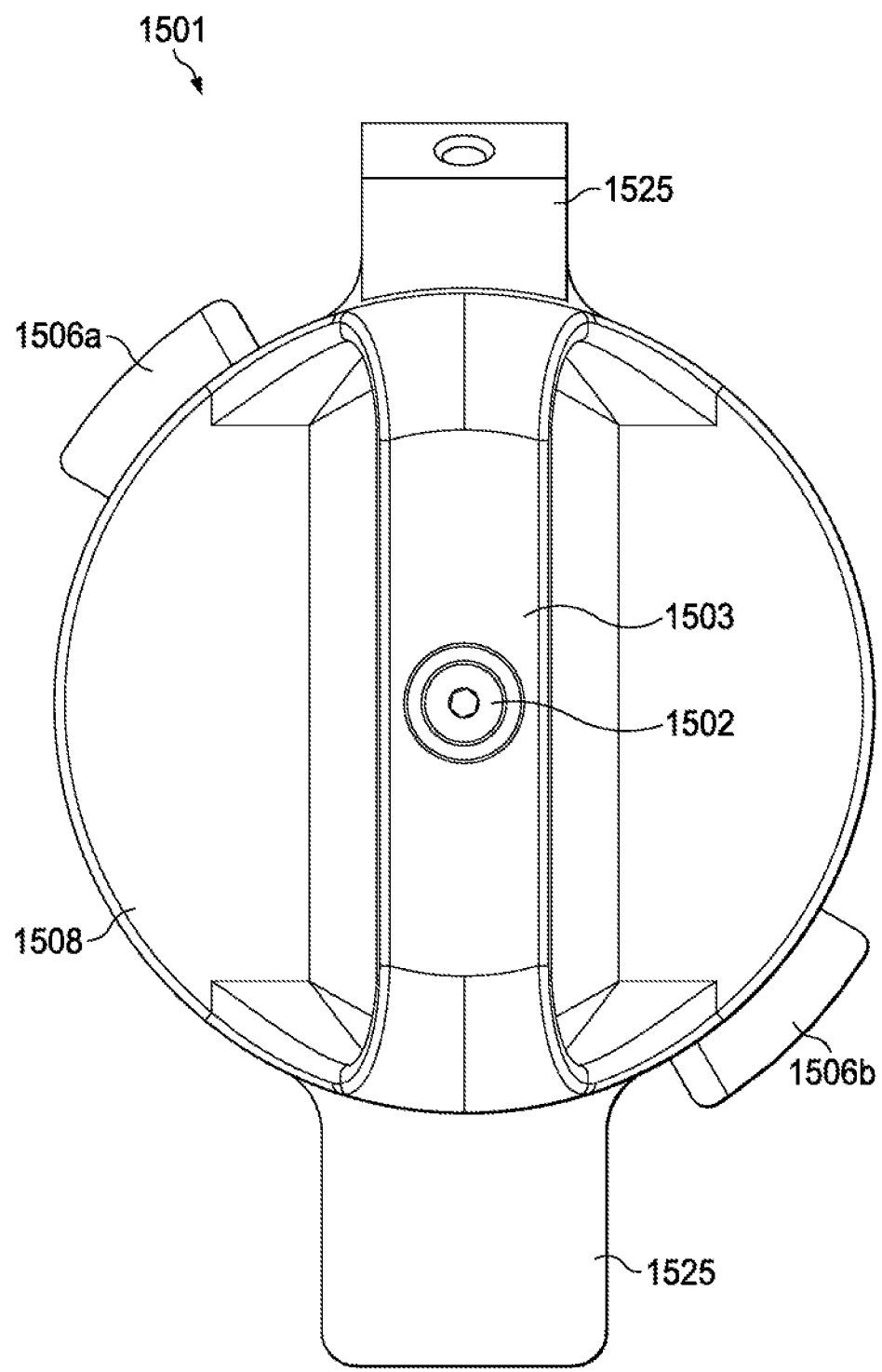
FIGS. 20A, 20B, and 20C are front, side, and back views, respectively, of the module of FIG. 19.
Figure 20B:
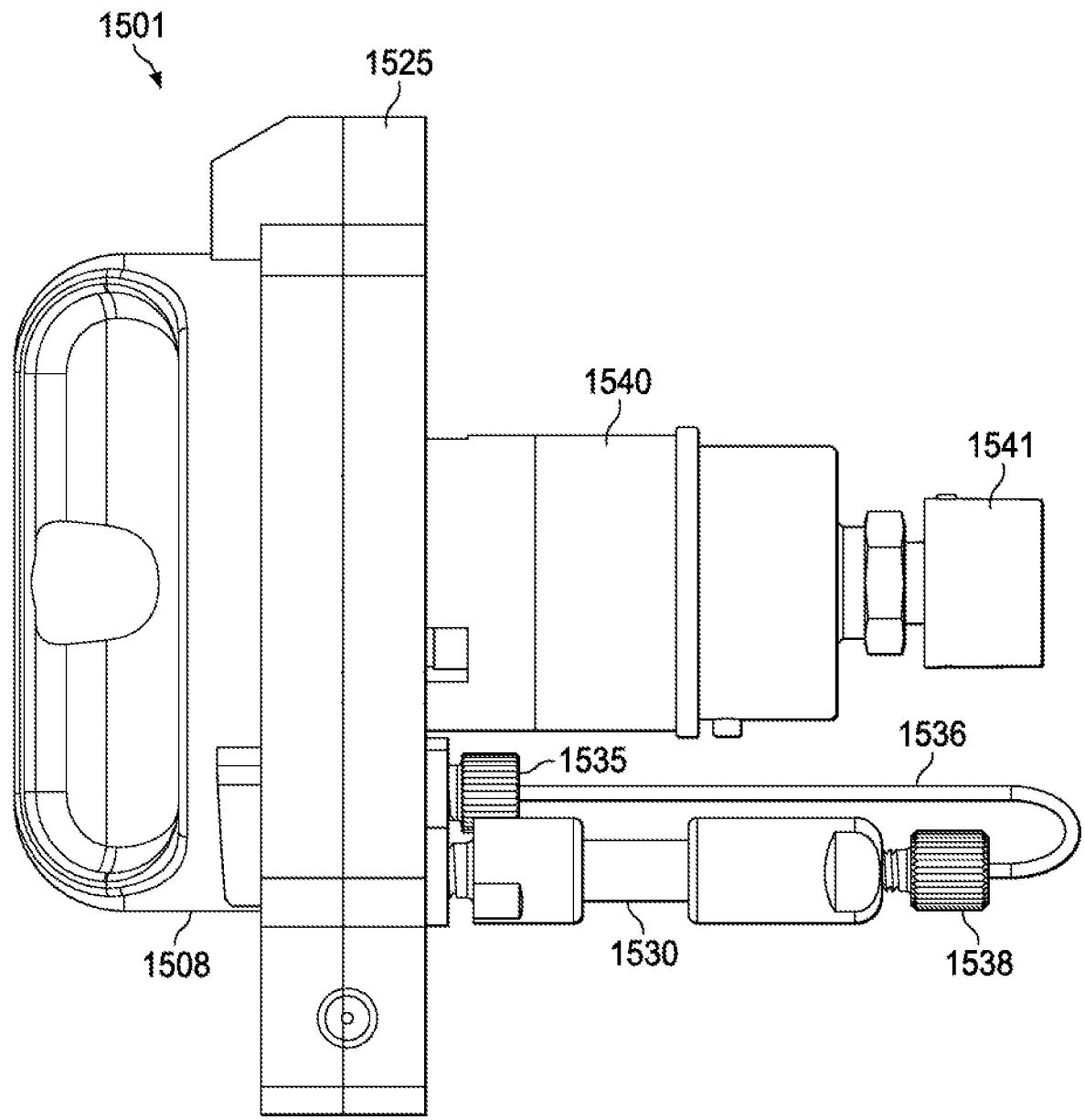
Figure 20C:
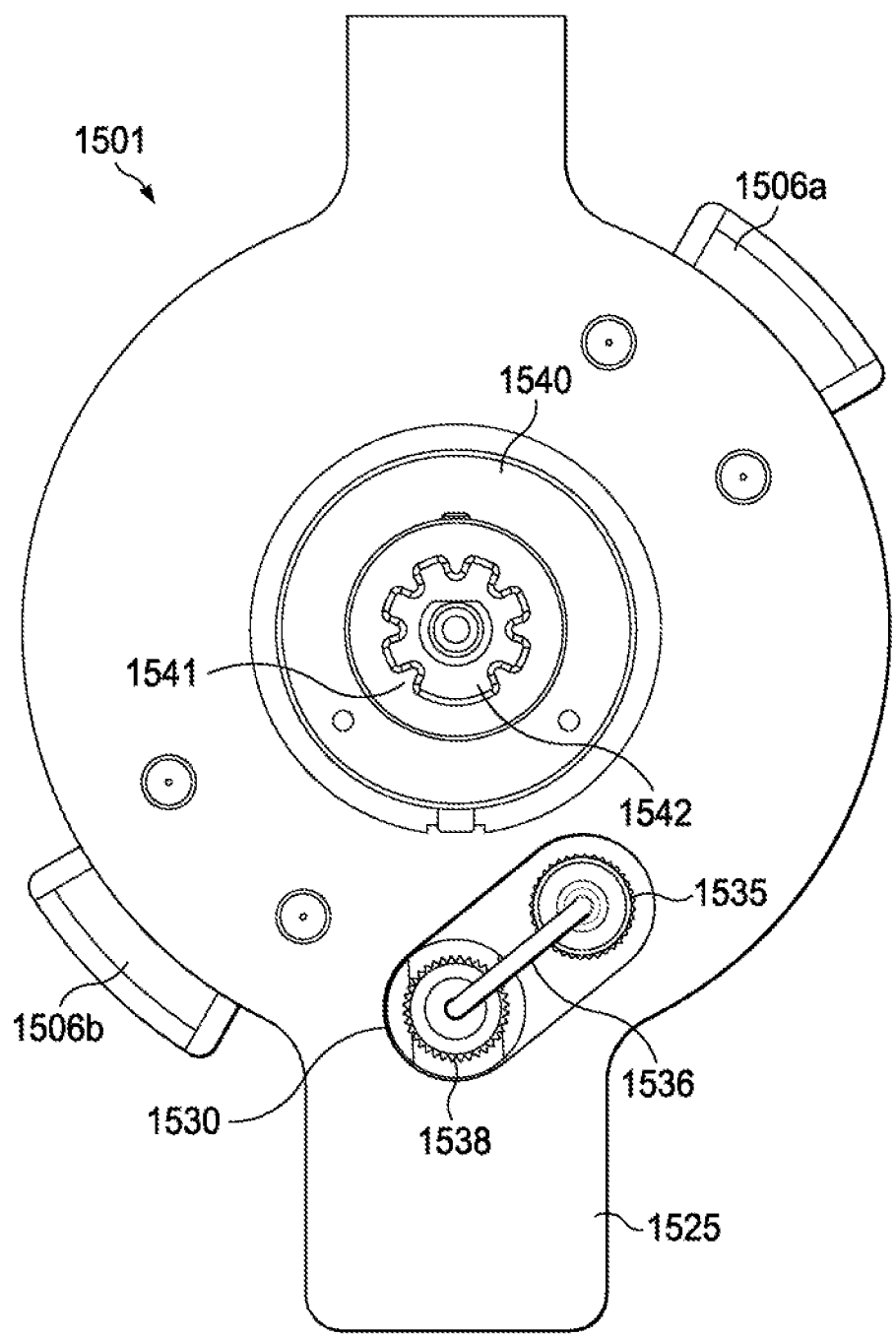

Now referring to FIGS. 20A, 20B, and 20C, front, side, and back views, respectively, of the module 1501 are provided, with the module 1501 shown in an assembled form. In FIG. 20A, it can be seen that the module 1501 is generally circular in shape, with portions of the manifold 1525 extending radially outwardly therefrom. In addition, projections 1506*a* and 1506*b* extend radially outwardly from the top portion 1508 of the module 1501.

In FIG. 20B, the valve 1540 has a first end which is attached to one side of the manifold 1525, while the second end of the valve 1540 extends longitudinally towards the end of the module 1501 away from the top portion 1508. In addition, the guard column 1535 is shown as removably attached to one side of the manifold 1525 (in this case the same side of the manifold 1525 to which the first end of the valve 1540 is attached). In addition, the column 1530 is attached to the same side of the manifold 1525 as the guard column in this example. Tubing 1536 connects one end of the guard column 1535 with one end of the column 1530. As shown in FIG. 20B, the second end of the valve 1540 may include a stem portion or shaft union 1541, which is adapted to cooperate with a rotating member (not shown) of the device 1500 when the module 1501 is placed into the nest 1510 and the nest 1510 is in a closed position, such that the device 1500 is operable to rotate the valve automatically in accordance with instructions executed by the control system of the device 1500.

FIG. 20C illustrates the second end of the module 1501 in a back view. As shown in FIG. 20C, the module 1501 has a generally circular shape with projections 1506*a*, 1506*b* extending radially outwardly and with portions of the manifold 1525 also extending radially outwardly. The guard column 1535 and column 1530 are attached to ports on the second side of the manifold 1525 and are connected to one another for fluid communication via tubing 1536. The tubing 1536, guard column 1535, and column 1530 may be removably connected to one another and/or to the ports on the second side of the manifold 1525 via any one of a number of fitting assemblies. The back side of the shaft union 1541 of the valve 1540 is shown as having a recessed area 1542. The recessed portion 1542 has a shape that is adapted to mate and cooperate with a projecting portion (not shown) of a rotor in the device 1500. As shown in FIG. 20C, the recessed area 1542 may have an irregular shape so that when it is in a mating and cooperating contact with the projecting portion of a rotor in the device 1500, and the rotor turns, the rotor of the valve 1540 will also turn without slippage. The projecting portion of the rotor of the valve 1540 also may have an irregular shape and be adapted to cooperate with the recessed area 1542 so that they can only be joined together in one way. This helps ensure that the valve 1540 is in the correct position.

Figure 21A:
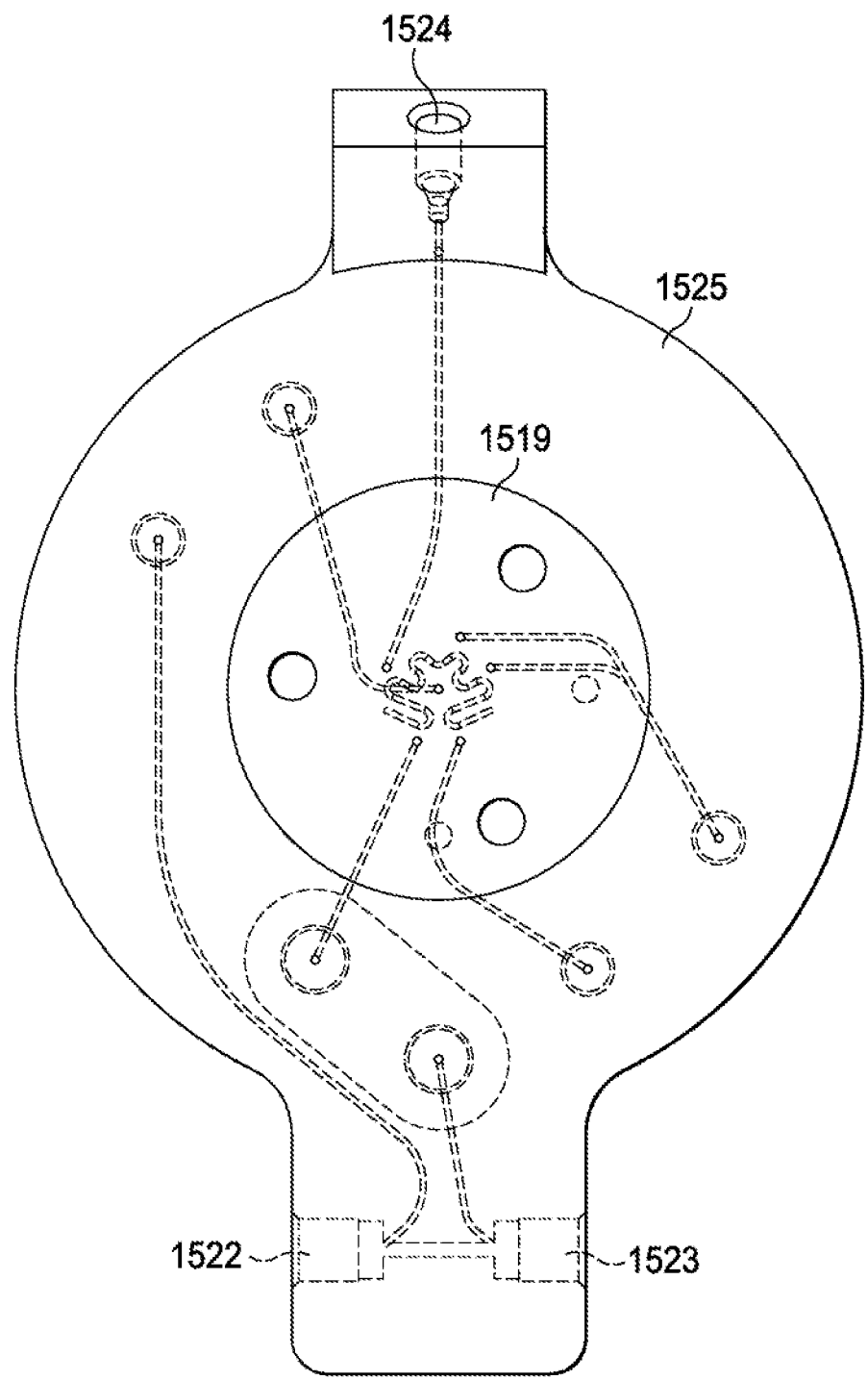
FIGS. 21A, 21B, and 21C are front, side, and back views, respectively, of a manifold of the module of FIG. 19.
Figure 21B:
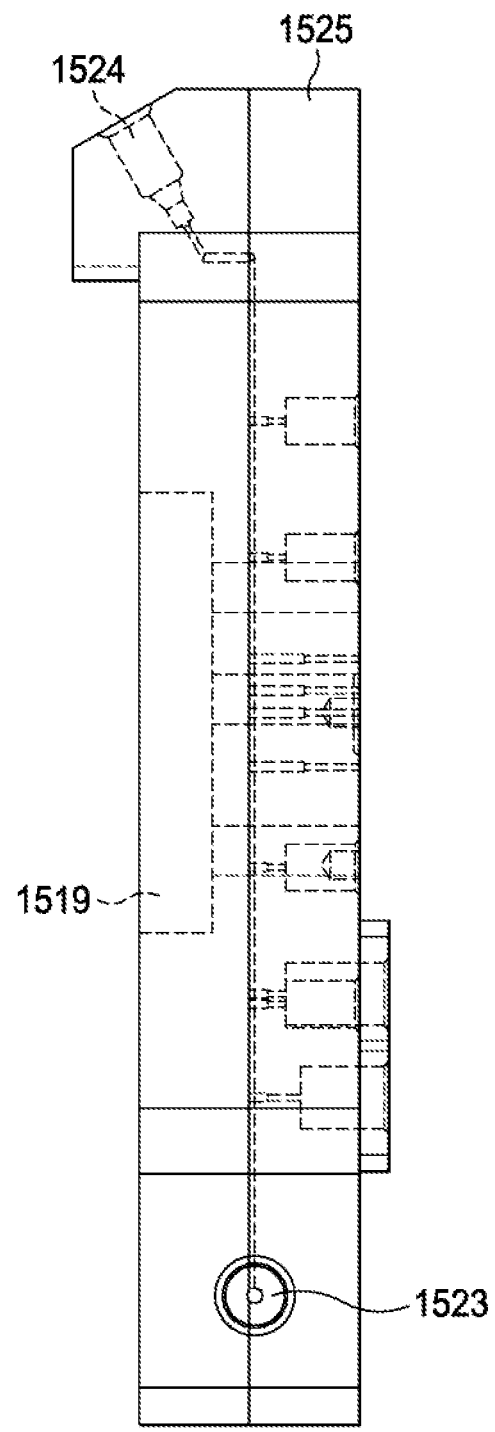
Figure 21C:
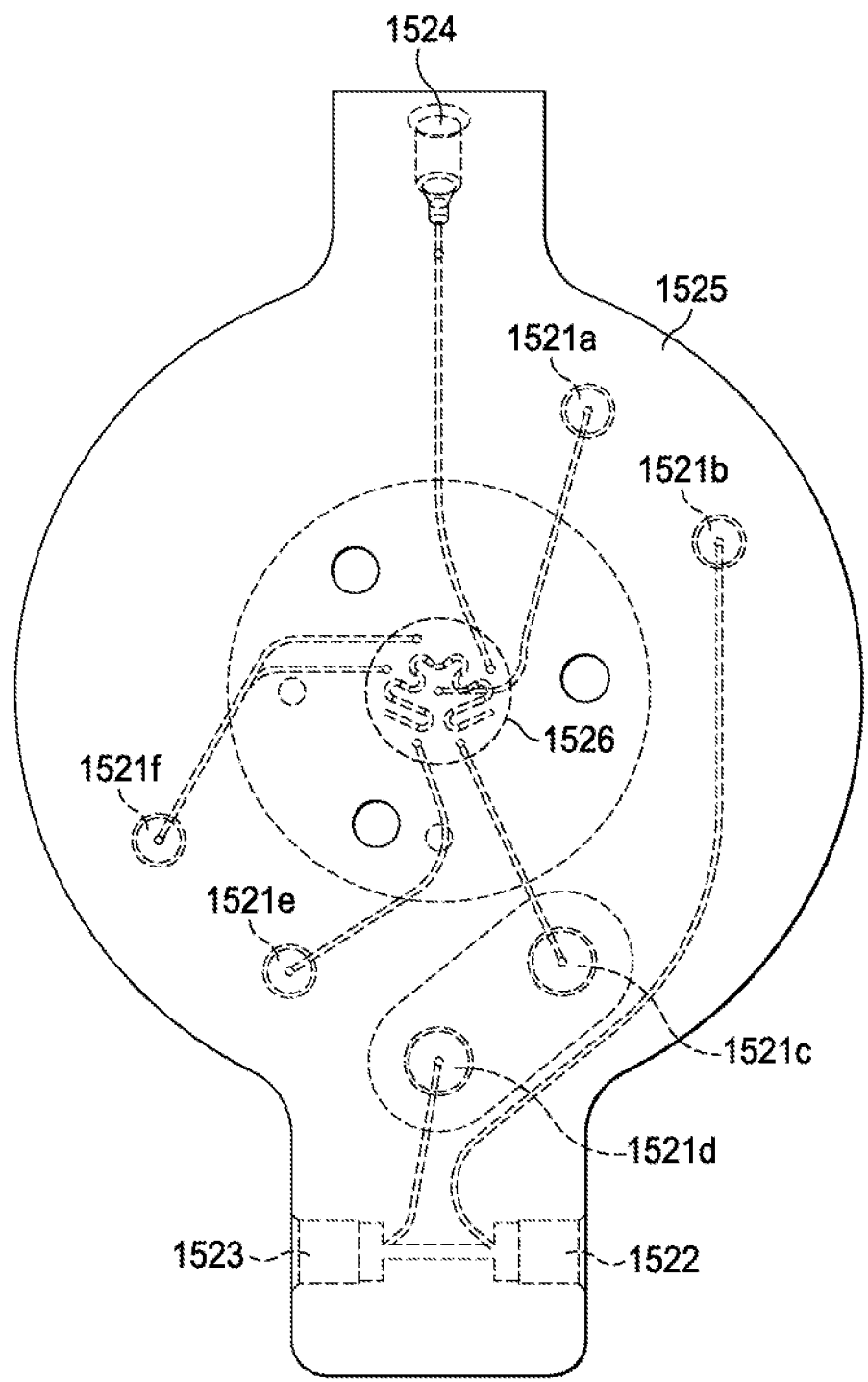

FIGS. 21A, 21B, and 21C provide additional views and details of the manifold 1525. FIGS. 21A, 21B, and 21C provide front, side, and back views, respectively, of the manifold 1525. As shown in FIG. 21A, the manifold 1525 includes an opening 1524 in one of the radially projecting portions. Opening 1524 is a port which can be adapted to removably receive a fitting assembly and tubing (not shown) and can be used for, among other things, a sample inlet. As indicated by the dashed lines in FIGS. 21A, 21B, and 21C, the manifold 1525 includes therein a number of fluid channels or pathways, as explained further below. The manifold 1525 also includes two opposing openings 1522 and 1523 in the second radially projecting portion of the manifold. These two openings 1522 and 1523 may be adapted to removably receive inputs, such as by having opening 1522 receive a source input (not shown) and having opening 1523 receive a detector input (not shown). The manifold also includes a recessed portion 1519 on its front side for receiving and holding one side of the handle mount 1520 therein.

FIG. 21B also shows the recessed portion 1519 on the front side of the manifold 1525, as well as the opening 1523, the port 1524, and the various fluidic pathways within the body of the manifold 1525 (shown in dashed lines in FIG. 21B).

In FIG. 21C, the port 1524 and the openings 1522, 1523 of the manifold 1525 are shown. In addition, FIG. 21C illustrates a number of additional openings in the back side of the manifold 1525. The manifold 1525 illustrated in FIG. 21C includes openings 1521*a*, 1521*b*, 1521*c*, 1521*d*, 1521*e*, and 1521*f*. In addition, this side of the manifold 1525 includes eight openings 1526 located near the center of the manifold 1525, within the circle 1526 drawn to highlight these openings 1526. The openings 1526 are located in a generally circular pattern near the center of the manifold 1525 in this example, including one opening located generally within the center of the other seven openings. These openings 1526 are adapted to provide fluid pathways when the front end of the valve 1540 is secured to the back side of the manifold 1525, with the fluid pathways selectable by rotation of a rotary in the valve 1540. Also shown in FIG. 21C is a serpentine pathway, which may extend between two of the openings 1526. In this particular example, the serpentine pathway serves as a sample loop for the fluid, and may be a groove that is etched, cut, or otherwise formed in the face of the manifold 1525.

Still referring to FIG. 21C, the following is an example of how the manifold may be connected to various fluidic inputs and outputs. In this example, port 1524 can be connected to a sample source and serves as a sample inlet to the manifold 1525. As noted above, the openings 1523 and 1522 can be connected to a source input and a source detector, respectively. In addition, opening 1521a can be connected to a first solvent source, opening 1521b can be connected to a waste receptacle, opening 1521c can be connected to a guard column, opening 1521d can be connected to a column, opening 1521e can be connected to a second solvent source, and opening 1521f can be connected to a waste receptacle. As noted, the openings 1526 can be connected to corresponding openings on a stator of the valve 1540 when the valve 1540 is attached to the back end of the manifold 1525. When the rotor of the valve 1540 is turned, different fluidic connections between the valve 1540 and the openings 1526 of the manifold 1540 can be selected.

Now referring to FIG. 22, an exploded view of a module 2201 in accordance with the present disclosure is provided. The module 2201 may comprise a top piece 2208, a handle mount 2220, a manifold 2225, a column 2230, a guard column 2235, and a valve 2240. A screw 2202 may be used to securely fasten the module top 2208 to the handle mount 2220. In addition, screws 2215 may be used to securely fasten the handle mount 2220, the manifold 2225, and the valve 2240 together. The guard column 2235 can be attached by tubing 2236 and fitting assemblies 2233 and 2234 to a first end of the column 2230, with the second end of the column 2230 to be attached to the back side of the manifold 2225. It should be noted that the guard column 2235 and the column 2230 may be selected for a particular module 2201 that, in turn, is intended for use in a particular application, such as may involve higher or lower pressures, one or more solvents with different chemical properties, one or more types of samples, and so forth. The top piece 2208 of the module 2201 includes two opposing projections (only projection 2206a is shown in FIG. 22). These projections 2206a, 2206b may be adapted to cooperate with and removably fit in cooperating notches to removably lock the module 2201 in place, the notches 2205a, 2205b of the nest 2210. As indicated by the threaded end portions of the fitting assembly 2233 and the column 2230, these ends may be removably and securely attached to the back side of the manifold 2225 by screwing the threaded end portions of the fitting assembly 2233 and/or column 2230 into corresponding openings in the back side of the manifold 2225 with internal threads adapted to removably receive and securely hold such end portions.

Similar to the manner in which the module 1501 can be secured in the nest 1510 (or removed therefrom) as explained above, the module 2201 and projections 2206a and 2206b can be adapted to travel along a helical groove (not shown) when the handle 2203 of the module 2201 is rotated, with the projections 2206a and 2206b traveling along the groove and pulling the module 2201 lower into the nest relative to the exterior surface of the nest until module 2201 is secured therein. Likewise, rotation of the handle 2203 in the opposite direction will result in the projections 2206a and 2206b reversing their path along the helical groove and raising the module 2201 until it can be pulled from the nest. Likewise, the fluidic connections for sealing tubing may be made in the same or similar manner as described above with respect to the securing of module 1501 in nest 1510.

Figure 23A:
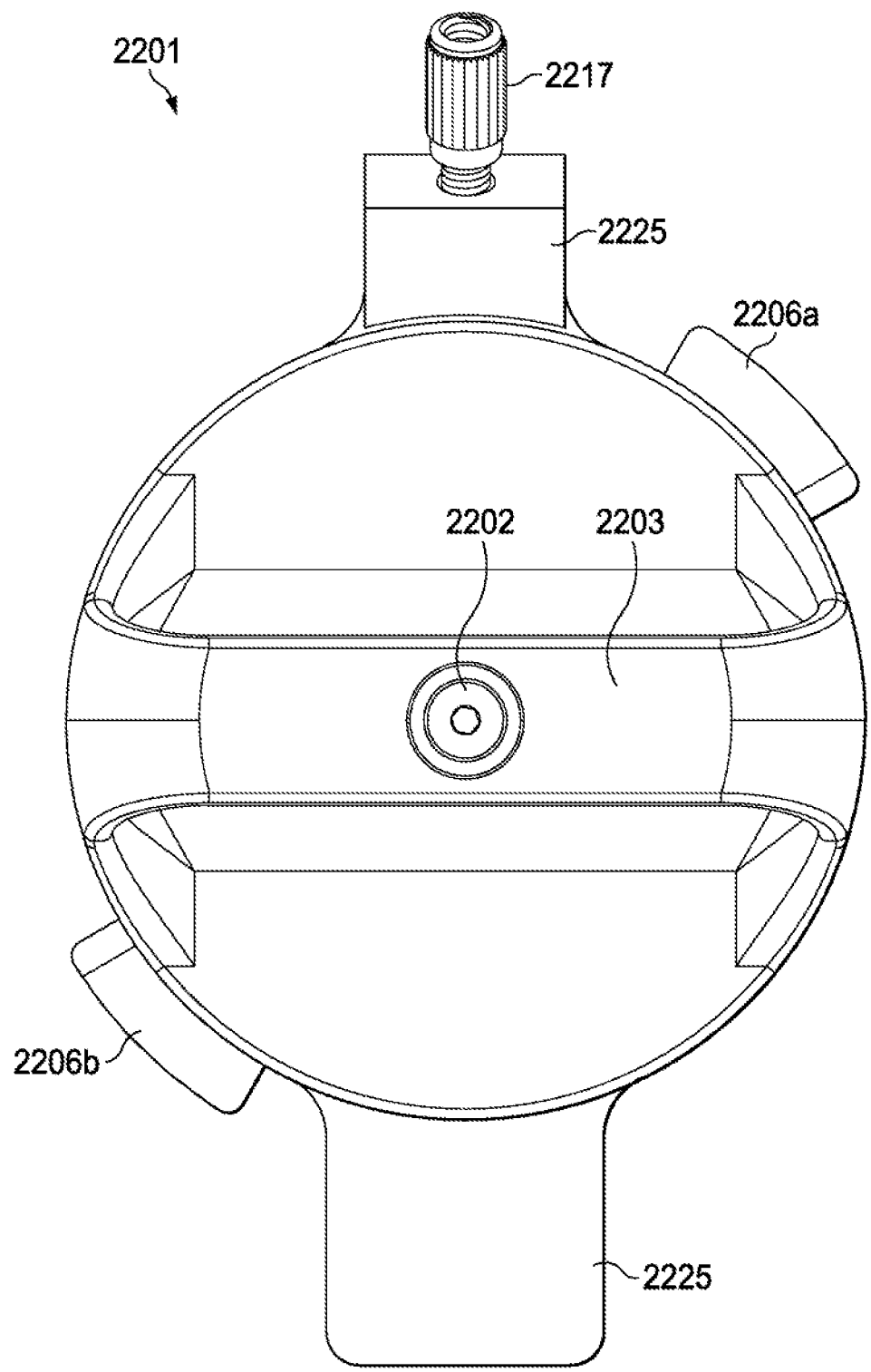
FIGS. 23A, 23B, and 23C are front, side, and back views, respectively, of the module of FIG. 22.
Figure 23B:
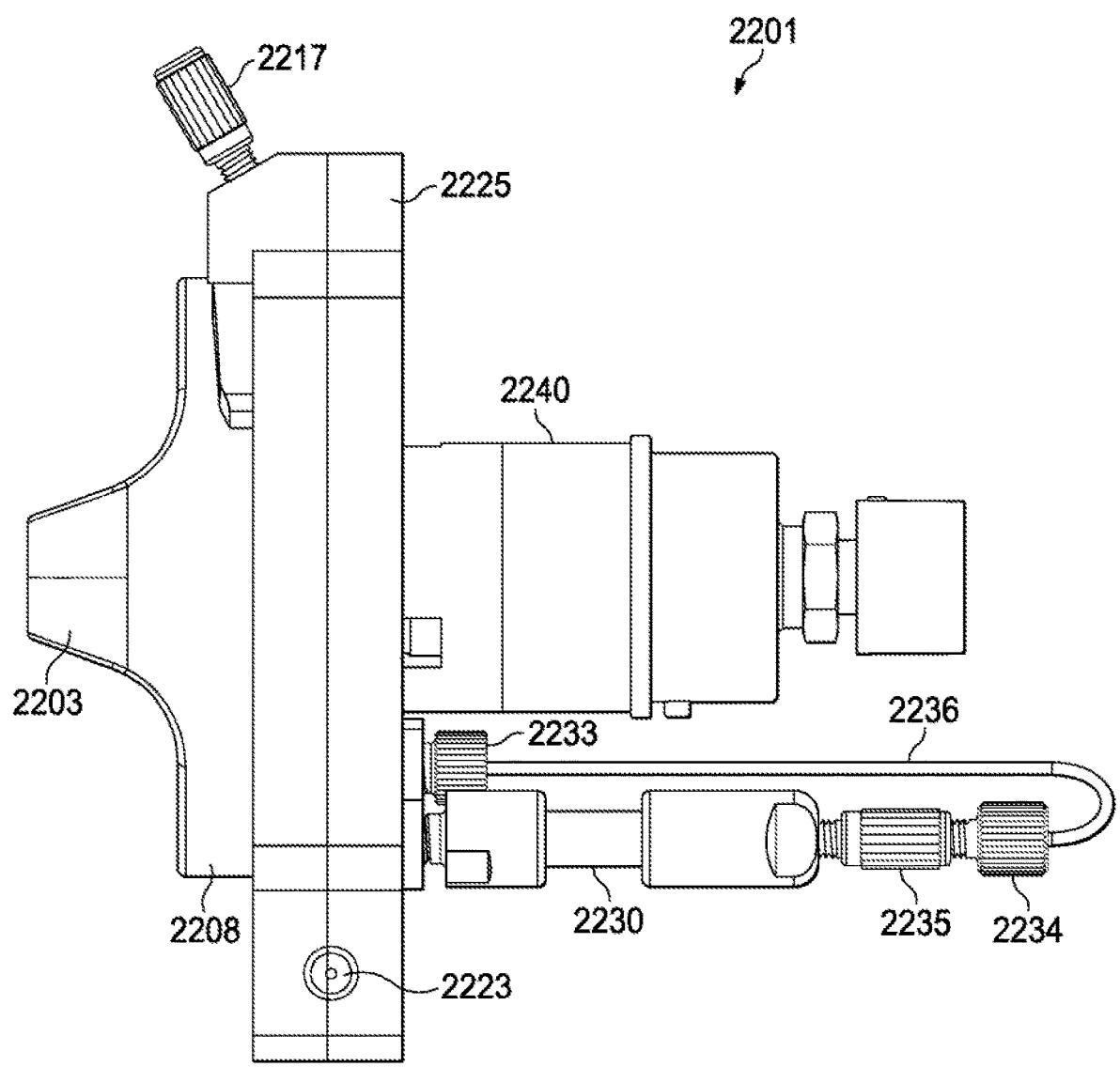
Figure 23C:
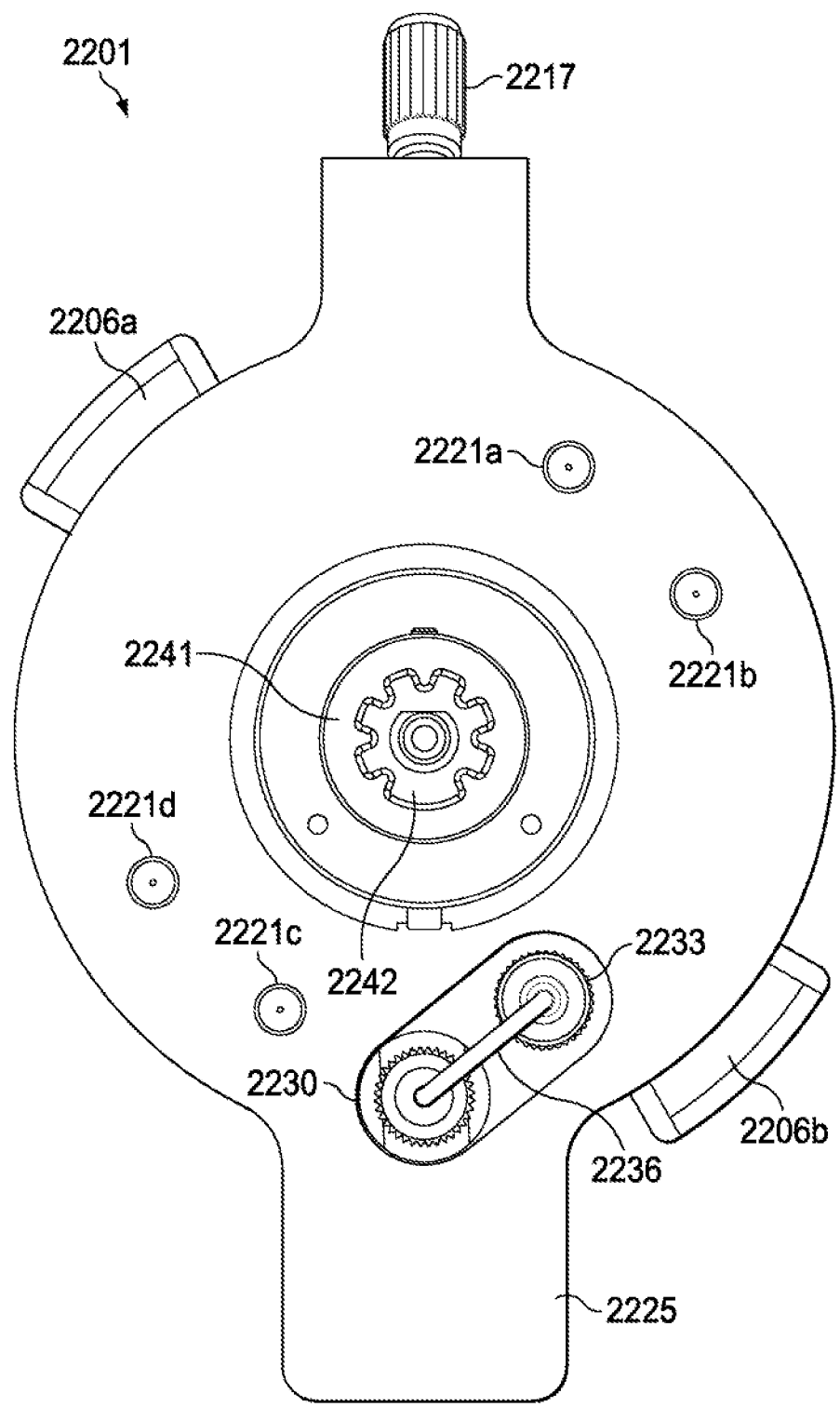

Now referring to FIGS. 23A, 23B, and 23C, front, side, and back views, respectively, of the module 2201 are provided, with the module 2201 shown in an assembled form. In FIG. 23A, it can be seen that the module 2201 is generally circular in shape, with portions of the manifold 2225 extending radially outwardly therefrom. In addition, projections 2206a and 2206b extend radially outwardly from the top portion 2208 of the module 2201.

In FIG. 23B, the valve 2240 has a first end which is attached to one side of the manifold 2225, while the second end of the valve 2240 extends longitudinally towards the end of the module 2201 away from the top portion 2208. In addition, the guard column 2235 is shown as removably attached to one side of the manifold 2225 (in this case the same side of the manifold 2225 to which the first end of the valve 2240 is attached). In addition, one end of the guard column 2235 is attached to one end of the column 2230, with a second end of the column 2230 attached to the same side of the manifold 2225. Tubing 2236 connects one end of the guard column 2235 with an opening on the back face of the manifold 2225. As shown in FIG. 23B, the second end of the valve 2240 may include a stem portion or shaft union 2241, which is adapted to cooperate with a rotating member (not shown) of the device 1500 when the module 2201 is placed into the nest 2210 and the nest 2210 is in a closed position, such that the device 1500 is operable to rotate the valve in accordance with user input and/or instructions executed by the control system of the device 1500, such that the operation of the valve may be automatic and controlled by the control system of the device 1500

FIG. 23C illustrates the second end of the module 2201 in a back view. As shown in FIG. 23C, the module 2201 has a generally circular shape with projections 2206a, 2206b extending radially outwardly and with portions of the manifold 2225 also extending radially outwardly. The guard column 2235 and column 2230 are attached to one another, with one end of the column attached to a port on the second side of the manifold 2225. The tubing 2236, guard column 2235, and column 2230 may be removably connected to one another and/or to the ports on the second side of the manifold 2225 via any one of a number of fitting assemblies. The back side of the shaft union 2241 of the valve 2240 is shown as having a recessed area 2242. The recessed portion 2242 has a shape that is adapted to mate and cooperate with a projecting portion (not shown) of a rotor in the device 1500. As shown in FIG. 23C, the recessed area 2242 may have an irregular shape so that when it is in a mating and cooperating contact with the projecting portion of a rotor in the device 1500, and the rotor turns, the rotor of the valve 2240 will also turn without slippage. The projecting portion of the rotor of the device 1500 also may have an irregular shape, and the shapes of the projecting portion and the recessed portion 2242 may be adapted to cooperate with one another so that they can only be joined together in one way. This configuration helps ensure that the device 1500 is in the correct position.

It should be noted that, among other advantages of the present disclosure, the devices, modules, and manifolds disclosed herein can be made of materials which are biocompatible. The use of stainless steel components in various systems can have potential drawbacks in situations involving biological samples and processes. For example, the components in a biological sample may attach themselves to the wall of stainless steel tubing. This can present problems because the detector's measurements of a given biological sample may not accurately reflect the sample if some of the sample's components or ions remain in the tubing and do not reach the detector. In addition, ions from the stainless steel tubing may detach from the tubing and flow past the detector, thus leading to potentially erroneous results. Still another concern, which may be even more important, is that of protein binding. For example, the use of nickel-plated components may release $Ni_2$ and/or $Cu_2$ ions, which can be detected by the detector and thus provide erroneous or poor results. Hence, there is a need for biocompatible materials and connections through the use of one more materials that are biologically and/or chemically inert with respect to such biological samples and processes, as well as the mobile phase or solvent used with such samples and processes.

The devices, modules and manifolds of the present disclosure can be made of biocompatible materials, including the flow cell, column, inlet and outlet ports, fluid pathways, tubing, and so forth, thus providing a biocompatible device, module or manifold. The devices, modules, and manifolds of the present disclosure, and their components and fluid pathways, including tubing, inlet and outlet ports, flow cell, column, filter, and the like may be made of any one or more of the following materials, alone or in combination: ULTEM, PEEK, polypropylene, fluorinated ethylene propylene (FEP), and/or any combinations thereof.

All of the devices, apparatuses and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. For example, the devices 1400 and 1500 are shown and described with different ways of removably receiving a module. It should be noted that the device could simply provide a seat or other recess either wholly or partially within the device for removably receiving all or a portion of a module therein; a hinged nest and a movable drawer are only examples provided for convenient reference. For example, in one embodiment of the present disclosure (not shown), the device may be provided with a portion which includes a valve and manifold like those shown and described above, and which are adapted to removably receive one or more guard columns and/or columns, such as by a threaded connection (like those shown in FIGS. 19 and 22) or by a connection which may use a fitting assembly. In such an embodiment, the guard column(s) and/or column(s) may be removably attached and connected to a side of the manifold which faces outwardly from a housing of another device or system and is thus easily accessible to a user or operator. In this embodiment, the guard column and/or column may be easily removed and replaced without removing and replacing the entire module, as the manifold and valve may remain in place and attached to the remainder of the other device or system.

While the disclosure has shown and described various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein.

We claim:

1. A disposable module for testing samples comprising:
a module adapted to be removably connected to a sample device, wherein said module comprises:
a top having projections configured to engage with a portion of the sample device;
a manifold having a body with a first side and a second side defining a plurality of openings and one or more fluid pathways extending therethrough, wherein a first side of the manifold is coupleable with the top and at least one of the plurality of openings is a sample inlet for receiving a sample from a sample source;
a guard column and a first column, each column having a first end and an opposing second end, wherein the first end of each column is removably coupleable with one opening of the plurality of openings of the manifold and the second end of each column is coupled to the second end of the other column; and
a valve having a first end and a second end, wherein the first end has a stator and is rotatably coupleable with a second side of the manifold and the second end of the valve is removably engageable with the sample device, wherein when the first end of the valve is engaged with the manifold, the stator is in fluid communication with one or more openings of the plurality of openings of the manifold and provides a fluid pathway between one or more openings of the plurality of openings of the manifold, and wherein when the second end of the valve is engaged with the sample device the valve is configured to rotate in response to rotation of a portion of the sample device,
wherein the manifold is adapted to receive a sample through the sample inlet and, when a solvent is pumped under pressure into the manifold, move through the first column and the one or more fluid pathways of the manifold.

2. The disposable module according to claim 1 wherein the manifold, guard column, first column, and sample inlet port are connected by tubing within the manifold, and comprise one or more biocompatible materials.

3. The disposable module according to claim 1 wherein the sample comprises: protein concentration, spectral information, fluorescence, or a combination thereof.

4. The disposable module according to claim 1 wherein the valve is configured to, in response to rotation of the valve, change the fluid pathway between the manifold and the stator.

5. The disposable module according to claim 1 wherein one or more of the plurality of openings of the manifold are configured to engage with one or more fittings of the sample device and form a fluid pathway between the manifold and the sample device.

6. The disposable module according to claim 5 wherein at least one of the plurality of openings of the manifold is configured to form a fluid pathway with one or more of a source detector, a first solvent source, a second solvent source, or a waste detector.

7. The disposable module according to claim 1 wherein the manifold, the guard column, the first column, and the valve define a fluid pathway through said disposable module, and wherein the fluid pathway comprises biocompatible materials.

8. The disposable module according to claim 1 wherein at least one of the plurality of openings of the manifold is configured to, when the valve is engaged with the sample device, engage with a fitting positioned in the sample device.

9. The disposable module according to claim 1 wherein said disposable module is adapted to operate with fluid pressures up to at least 500 psi.

10. The disposable module according to claim 1 wherein at least one of the one or more fluid pathways of the manifold comprises a sample loop.

11. The disposable module according to claim 1 wherein, the first end of the valve comprises a stator defining a plurality of openings therethrough, the stator configured to rotate to form fluid connections between the manifold and the valve.

12. The disposable module according to claim 1 wherein said disposable module is adapted to operate with fluid pressures up to at least 15,000 psi.

13. The disposable module according to claim 1 wherein the second end of the valve comprises a stem configured to, when the module is engaged with sample device, engage with a rotor positioned in the sample device.

14. The disposable module according to claim 13 wherein, when the valve is engaged with the rotor, the rotor is configured to rotate the valve based on instructions received by the sample device.

15. The disposable module according to claim 13, wherein the stem has a first engagement surface having a first shape and the rotor has a second engagement surface having a second shape, and wherein the first and second engagement surfaces and coupleable with one another.

16. A portable device for a testing of samples comprising:
a portable device adapted to removably hold at least one solvent container in or on a first portion of said portable device and removably couple with at least one disposable module, wherein the portable device comprises a housing and a receiving port configured to receive the disposable module, wherein the portable device is further adapted to removably accept a connection from a sample source to allow the at least one disposable module to be connected to the sample source, wherein the portable device further comprises a control system having a processor, memory, instructions executable by said processor, and a display panel adapted to receive inputs from a user and adapted to display information to a user; and wherein the disposable module comprises:
a manifold having a body with a first side and a second side defining a plurality of openings and one or more fluid pathways extending therethrough, wherein a first side of the manifold is coupleable with a top and at least one of the plurality of openings is a sample inlet for receiving a sample from the sample source;
a guard column and a first column, each column having a first end and an opposing second end, wherein the first end of each column is removably coupleable with one opening of the plurality of openings of the manifold and the second end of each column is coupled to the second end of the other column; and
a valve having a first end, a second end, wherein the first end has a stator and is rotatably coupleable with a second side of the manifold and the second end of the valve is removably engageable with the portable device, wherein when the first end of the valve is engaged with the manifold, the stator is in fluid communication with one or more openings of the plurality of openings of the manifold and provides a fluid pathway between one or more openings of the plurality of openings of the manifold, and wherein when the second end of the valve is engaged with the portable device the valve is configured to rotate in response to rotation of a portion of the portable device,
wherein the manifold is adapted to receive a sample through the sample inlet and, when a solvent is pumped under pressure into the manifold, move through the first column and the one or more fluid pathways of the manifold.

17. The portable device according to claim 16 wherein the display panel is coupled to said control system and is adapted to allow the user to select any one or more of the following parameters to be executed by said control system: flow rate, sampling timing, sample volume, sampling rate, solvent selection, sample to be tested, or a combination thereof.

18. The portable device according to claim 17 wherein the display panel is adapted to display information relating to the one or more parameters.

19. The portable device according to claim 16 further comprising a data port coupled to said control system and adapted to allow a user to input data to said control system, to obtain data from said control system, or a combination thereof.

20. The portable device according to claim 16 wherein said portable device, together with the at least one disposable module and the at least one solvent container, weighs from about 2.5 Kilograms to about 22 Kilograms, with the solvent container containing about 0.5 liters to about 4 liters of fluid.

21. The portable device according to claim 16 wherein said portable device is adapted to operate with fluid pressures up to at least 500 psi.

22. The portable device according to claim 16 wherein when the second end of the valve is engaged with the portable device the valve is configured to rotate in response to rotation of a portion of the portable device.

23. The portable device according to claim 16 wherein the valve is configured to, in response to rotation of the valve, change the fluid pathway between the manifold and the second end of the valve.

24. The portable device according to claim 16 wherein the portable device further comprises a rotor and the second end of the valve comprises a stem configured to, when the disposable module is engaged with portable device, engage with the rotor.

25. The portable device according to claim 24 wherein when the valve is engaged with the rotor, the processor of the portable device is configured to rotate the rotor based on instructions received by the processor.

26. The portable device according to claim 16 further comprising a portion adapted to removably hold at least one battery and to removably couple said battery to said control system.

27. A module for analysis of a sample, comprising:
a valve having a stator with a first plurality of openings on one side thereof;
a column having a first end and a second end; and
a manifold having a first side and a second side, wherein the first side has a second plurality of openings, each corresponding to one of the plurality of first openings, and the first side has a third plurality of openings, with at least one of the third plurality of openings in fluid communication with the second end of the column and at least another one of the third plurality of openings in fluid communication with one or more of a solvent source and a waste receptacle, and wherein the manifold further comprises a flow cell and has first and second flow cell openings, wherein the first flow cell opening in the manifold is adapted to receive a source input to the flow cell and the second flow cell opening is adapted to receive a detector input to the flow cell, and wherein the module is adapted to be removably attached wholly or partially to a device.

28. The module according to claim 27, wherein the flow cell is adapted to be connected to at least one or more instruments for determining a characteristic of a sample, and wherein the characteristic of the sample comprises: protein concentration, spectral information, fluorescence, or a combination thereof.

29. The module according to claim 27, wherein the module further comprises biocompatible fluid pathways therein.

30. The module according to claim 27 wherein the module is further adapted to be connected to a control system when attached to the device.

31. The module according to claim 27 wherein the module is adapted to fit at least partially in a nest of the device.

32. The module according to claim 27 wherein the module is adapted to fit at least partially in a hinged nest of the device.

33. The module according to claim 27 wherein the module is adapted to removably fit at least partially in a recess or seat of the device.

34. The module according to claim 27 wherein the module weighs from about 0.1 Kilograms to about 3 Kilograms.

35. The module according to claim 27 wherein the module is adapted to operate with fluid pressures up to 500 psi, 6,000 psi, 9,000 psi, 15,000 psi, or 20,000 psi.

36. The module according to claim 27 wherein the manifold further comprises a sample inlet.

37. A device comprising:
a valve having a stator with a first plurality of openings on one side thereof; and a manifold having a first side and a second side, wherein the first side has a second plurality of openings, each corresponding to and adapted to be coupled to one of the first plurality of openings, and the first side or the second side has a third plurality of openings, with at least one of the third plurality of openings adapted for fluid communication with one end of a column when a column is removably coupled to the manifold, and at least another one of the third plurality of openings is adapted to be in fluid communication with one or more of a solvent source and a waste receptacle, and wherein the manifold further comprises a flow cell and has first and second flow cell openings, wherein the first flow cell opening in the manifold is adapted to receive a source input to the flow cell and the second flow cell opening is adapted to receive a detector input to the flow cell, wherein the first side or the second side of the manifold is adapted to be removably attached wholly or partially to a guard column or a column, and wherein the valve and the manifold are located wholly or partially within a housing of a second device.

38. The device according to claim 37 wherein at least one of the second plurality of openings and the first plurality of openings, the at least one of the third plurality of openings and the one end of the column, and the first side or the second side of the manifold and the guard column or column, are coupled for fluid communication by tubing.

39. The device according to claim 37 wherein the second side of the manifold faces outwardly from the housing of the device.

40. The device according to claim 37 wherein the first side and the second side of the manifold comprise opposing sides of the manifold.

* * * * *